United States Patent [19]

Pearson et al.

[11] 4,407,815

[45] Oct. 4, 1983

[54] β-LACTAM ANTIBACTERIAL COMPOUNDS, THEIR PREPARATION AND PHARMACEUTICAL COMPOSITIONS CONTAINING THEM

[75] Inventors: Michael J. Pearson; Clive L. Branch, both of Horsham, England

[73] Assignee: Beecham Group Limited, England

[21] Appl. No.: 233,180

[22] Filed: Feb. 10, 1981

[30] Foreign Application Priority Data

Feb. 14, 1980 [GB] United Kingdom ............... 8005037

[51] Int. Cl.³ .................... C07D 487/04; A61K 31/40
[52] U.S. Cl. ............................... 424/274; 260/239 A; 260/245.2 T; 424/114; 424/263; 424/274; 546/272
[58] Field of Search ................ 260/245.2 T; 546/272; 424/274, 263

[56] References Cited

FOREIGN PATENT DOCUMENTS 1627 10/1978 European Pat. Off. .
1628 10/1978 European Pat. Off. .
8888 8/1979 European Pat. Off. .

Primary Examiner—Mary C. Lee
Attorney, Agent, or Firm—Jacobs & Jacobs

[57] ABSTRACT

The present invention provides the compounds of the formula (II):

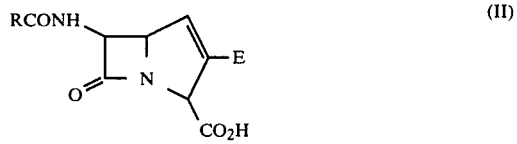

and pharmaceutically acceptable salts and cleavable esters thereof wherein RCONH is an organic acylamino group and E is a carboxy group or pharmaceutically acceptable salt or ester thereof or is a cyano group. Their preparation is described as is their use in compositions containing them. Compounds wherein RCONH is replaced by an azido group are described as useful intermediates.

103 Claims, No Drawings

β-LACTAM ANTIBACTERIAL COMPOUNDS, THEIR PREPARATION AND PHARMACEUTICAL COMPOSITIONS CONTAINING THEM

This invention relates to novel β-lactam antibacterial agents, their preparation and their use, and in particular to 7-oxo-1-azabicyclo[3.2.0]hept-3-enes.

Published European patent application Nos. 0008888, 0001627, 0001628 and U.S. Pat. No. 4,146,633 disclose compounds of the general formula (I):

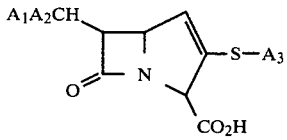 (I)

and salts and esters thereof wherein $A_1$, $A_2$ and $A_3$ independently are substituted organic groups. A new series of acylamino isocarbapenem compounds has now been discovered that possesses antibacterial activity.

When used herein the trivial term isocarbapenem refers to the 7-oxo-1-azabicyclo[3.2.0]hept-3-ene ring system.

The present invention provides the compounds of the formula (II):

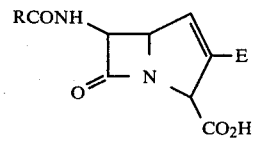 (II)

and pharmaceutically acceptable salts and cleavable esters thereof wherein RCONH is organic acylamino group, and E is a carboxy group or pharmaceutically acceptable salt or $C_{1-10}$ alkyl or substituted $C_{1-10}$ alkyl ester thereof or is a cyano group.

Preferably E is a $C_{1-10}$ alkoxycarbonyl or substituted $C_{1-10}$ alkoxycarbonyl or cyano group.

Certain suitable values of E are those of the sub-formulae (L) and (M):

 (L)

 (M)

wherein $B_1$ is an alkyl group of 1 to 6 carbon atoms optionally substituted by an alkoxy or alkanoyloxy group of 1 to 7 carbon atoms, $B_2$ is an alkenyl or alkynyl group of up to 5 carbon atoms or is a phenyl group optionally substituted by a fluorine, chlorine, bromine, nitro or alkyl or alkoxy of up to 4 carbon atoms; and $B_3$ is a hydrogen atom, an alkyl group of up to 4 carbon atoms or is a phenyl group optionally substituted by a fluorine, chlorine, bromine, nitro or alkyl or alkoxy of up to 4 carbon atoms.

More suitably $B_1$ is an alkyl group of 1 to 6 carbon atoms.

More suitably $B_1$ is a methyl, ethyl, propyl, isopropyl, butyl, isobutyl, sec-butyl, tert-butyl, pentyl, neopentyl, isopropyl or hexyl group.

In particular $B_1$ is a methyl, ethyl or propyl group.

A preferred value for $B_1$ is a methyl group.

More suitably $B_2$ is a hydrogen atom and $B_3$ is a phenyl group optionally substituted by a fluorine, chlorine, bromine, nitro or alkyl or alkoxy of up to 4 carbon atoms.

In particular $CHB_2B_3$ is a benzyl, methoxybenzyl ethoxybenzyl, nitrobenzyl or chlorobenzyl group.

A preferred value for E is a cyano group.

Suitably RCONH is an organic acylamino group such as is found in antibacterially effective penicillins and cephalosporins. Thus suitable groups RCONH include those of sub-formulae (a), (b) (c) and (d):

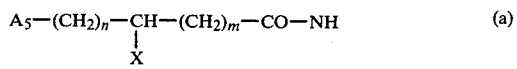 (a)

 (b)

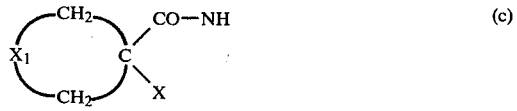 (c)

 (d)

wherein n is 0, 1 or 2; m is 0, 1 or 2; $A_5$ is an alkyl group of 1 to 6 carbon atoms, a cycloalkyl group of 3 to 6 carbon atoms, cyclohexenyl, cyclohexadienyl, phenyl hydroxyphenyl, thienyl or pyridyl group; X is a hydrogen, bromine or chlorine atom, a carboxylic acid, carboxylate ester, hydroxy, aycloxy amino, heterocyclylamino, ureido, guanidino or acylureido group; $A_6$ is an aromatic group such as a phenyl, 2,5-dimethoxyphenyl, 2-alkoxy-1-naphthyl, 3-arylisoxazolyl, isothiazolyl or 3-aryl-5-methylisoxazolyl group; $X_1$ is a $CH_2OCH_2$, $CH_2SCH_2$ or $(CH_2)_n$ group; and $X_2$ is an oxygen or sulphur atom. For example, phenylacetamido, p-hydroxyphenylacetamido, o-hydroxyphenylacetamido, m-hydroxyphenylacetamido, α-chlorophenylacetamido, α-bromophenylacetamido, α-carboxyphenylacetamido and esters thereof such as the methylphenyl, indanyl and phenyl esters, α-azidophenylacetamido, α-aminophenylacetamido, α-hydroxyphenylacetamido, α-ureidophenylacetamido, α-guanidinophenylacetamido, α-(acetylureido)-phenylacetamido, α-acetoxyphenylacetamido, α-tetrazolylphenylacetamido, acetamido, chloroacetamido, bromoacetamido, propionamido, pyridylacetamido, 2-thienylacetamido, 3-thienylacetamido, 2-thienylpropionamido, 3-thienylpropionamido, α-chloro (p-hydroxyphenyl)acetamido, α-bromo(p-hydroxyphenyl)acetamido, α-carboxy(p-hydroxyphenyl)acetamido and esters thereof such as the methylphenyl, indanyl and phenyl esters α-amino(p-hydroxyphenyl)acetamido, α-hydroxy(p-hydroxyphenyl)acetamido, α-acetoxy(p-hydroxyphenyl)acetamido, α-ureido[p-hydroxyphenyl]acetamido, α-guanidino (p-hydroxyphenyl)acetamido, α-acetylureido(p-hydroxyphenyl)acetamido, phenoxyacetamido, o-hydroxyphenoxyacetamido, m-hydroxyphenoxyacetamido, p-hydroxyphenoxyacetamido, methoxyacetamido, ethoxyacetamido, α-amino(p-hydroxy)phenoxyacetamido, α-aminophenoxyacetamido, α-acetylphenoxyacetamido, α-acetyl(p-hydroxy)phenylacetamido, α-hydroxyphenoxyacetamido, α-hydroxy(p-hydroxy)-phenylacetamido, α-carboxyphenoxyacetamido and esters thereof such as the methylphenyl, indanyl and phenyl esters, α-carboxy(p-hydroxy)phenoxyacetamido and esters thereof such as the methylphenyl, indanyl and phenyl esters, phenoxypropionamido, phenoxybutyramido, benzamido, 2,6-dimethoxybenzamido, 2-ethoxy-1-naphthamido, 2-methoxy-1-naphthamino, 2-propoxy-1-naphthamido, 3-phenyl-5-methyl-4-isoxazolylcarboxyamido, 3-o-chlorophenyl-5-methyl-4-isoxazolylcarboxamido, 3-o,o-dichlorophenyl-5-methyl-4-isoxazolylcarboxyamido, isothiazolylcarboxamido, 3-o,o-fluorochlorophenyl-5-methyl-4-isoxazolylcarboxamido, 3-phenyl-4-isoxazolylcarboxamido, 3-o-chlorophenyl-4-isoxazolylcarboxamido, 3-o,o-dichlorophenyl-4-isoxazolylcarboxamido, 3-o,o-fluorochlorophenyl-4-isoxazolylcarboxamido, 1-aminocyclohexyl-1-carboxamido, phenylthioacetamido, phenylthiopropionamido, p-hydroxyphenylthioacetamido, and the like.

More suitably groups R COHN include those of the sub-formulae (e) and (f):

$$R^2-CH-CO-NH \quad (e)$$
$$\quad | \quad$$
$$\quad R^3$$

$$R^4-CH-CO-NH \quad (f)$$
$$\quad | \quad$$
$$\quad R^5$$

wherein $R^2$ is a phenyl, thienyl or phenoxy group; $R^3$ is a hydrogen atom or methyl group; $R^4$ is a phenyl, p-hydroxyphenyl, thienyl or cyclohexadienyl group; and $R^5$ is a hydroxy, amino or carboxylic acid group or phenyl, methylphenyl, indanyl, or $C_{1-6}$ alkyl ester thereof.

A particularly preferred group of the sub-formula (e) is the phenoxyacetamido group. Another particularly preferred group of the sub-formula (e) is the phenylacetamido group.

Other particularly suitable groups of the formula R CO—NH— include the α-methylphenoxyacetamido, α-methylphenylacetamido, α-methyl-2-thienylacetamido, α-methyl-3-thienylacetamido, 2-thienylacetamido, 3-thienylacetamido, α-hydroxyphenylacetamido, α-hydroxy(p-hydroxyphenyl)acetamido, α-hydroxy-2-thienylacetamido, α-hydroxy-3-thienylacetamido, α-aminophenylacetamido, α-amino(p-hydroxyphenyl)acetamido, α-amino-3-thienylacetamido, α-amino-2-thienylacetamido, α-carboxyphenylacetamido, α-carboxy(p-hydroxyphenyl)acetamido, α-carboxy-2-thienylacetamido, α-carboxy-3-thienylacetamido, the methyl, ethyl, propyl, butyl, phenyl, methylphenyl or indanyl ester of α-carboxyphenylacetamido, the methyl, ethyl, propyl, butyl, phenyl, methylphenyl or indanyl ester of α-carboxy (p-hydroxyphenylacetamido), the methyl, ethyl, propyl, butyl, phenyl, methylphenyl or indanyl ester of α-carboxy-2-thienylacetamido, and the methyl, ethyl, propyl, butyl, phenyl, methylphenyl or indanyl ester of α-carboxy-3-thienylacetamido.

It is evident from the foregoing that preferred compounds of this invention are those of formula (III):

PhO—CH$_2$—CONH (III)
(bicyclic β-lactam structure with E' and CO$_2$H substituents)

and pharmaceutically acceptable salts and cleavable esters thereof wherein E' is a methoxycarbonyl or cyano group.

Another preferred sub-group of compounds of this invention are those of the formula (IV):

PhCH—CONH (IV)
|
CO$_2$B
(bicyclic β-lactam structure with E' and CO$_2$H substituents)

and pharmaceutically acceptable salts and cleavable esters thereof wherein E' is a methoxycarbonyl or cyano group, and B is a cation, hydrogen atom or a benzyl, phenyl, methylphenyl or indanyl group.

Yet another preferred sub-group of compounds of this invention are those of the formula (V):

Ph—CH—CO—NH (V)
|
NH$_2$
(bicyclic β-lactam structure with E' and CO$_2$H substituents)

and pharmaceutically acceptable salts and cleavable esters thereof wherein E' is a methoxycarbonyl or cyano group.

Suitable pharmaceutically acceptable salts of the compounds of the formulae (II)–(V) include metal salts of example aluminium, sodium, potassium, calcium and magnesium, and ammonium or substituted ammonium salts.

An example of a particularly apt substituted ammonium salt is the p-toludiene salt.

Particularly apt metal salts are the sodium, potassium, calcium and magnesium salts.

A preferred salt is the sodium salt.

A preferred salt is the potassium salt.

The compounds of the formulae (II)–(V) are aptly in the form of a free acid. If a free amino group is present in the group RCONH and the carboxylate is in the form of a free acid then a zwitterion may be formed. For example the compound of the formula (V) may be depicted as a zwitterion.

If the group E in the compound of the formula (II) contains an ester group cleavable by hydrogenolysis as hereinbelow described, then a di-acid may be formed. Such di-acids may be presented in the form of a di-salt, suitable pharmaceutically acceptable salts for a carboxy group E' being as hereinbefore described. Cleavable esters of the compounds of the present invention include those cleavable by hydrogenolysis and those cleavable by ready hydrolysis in the human body.

Suitable esters that are cleavable by hydrogenolysis include benzyl esters wherein the phenyl part is optionally substituted by a lower alkyl group of 1 to 6 carbon atoms, a lower alkoxy group of 1 to 6 carbon atoms, a chlorine or bromine atom or a nitro group.

We have found the p-nitrobenzyl ester to be most suitable.

Esters cleavable by hydrogenolysis are most useful as intermediates to other compounds of this invention.

Suitable esters that are cleavable in the human body, that is to say in-vivo hydrolysable include those of sub-formulae (g), (h) and (j):

$$-CO-O-CHR_1-O-CO-R_2 \quad (g)$$

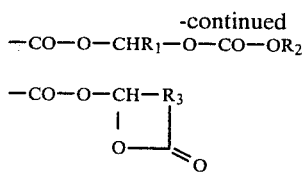    (h)

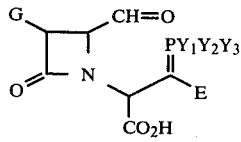    (VII)

wherein $R_1$ is a hydrogen atom or a methyl group, $R_2$ is an alkyl group of up to 4 carbon atoms or a phenyl or benzyl group and $R_3$ is a —CH=CH—, 1,2-phenylene or 4,5-dimethoxy-1,2-phenylene group.

Particularly apt in-vivo hydrolysable esters include the acetoxymethyl, pivaloyloxymethyl, α-acetoxyethyl, α-pivaloyloxyethyl, α-ethoxycarbonyloxyethyl, phthalidyl and 3,4-dimethoxyphthalidyl ester.

A preferred ester group is the phthalidyl ester.

The compounds of the formulae (II)–(V) are generally provided as racemic mixtures. It is believed that the optical isomer possessing greatest antibacterial activity is that depicted in the compound of the formula (VI):

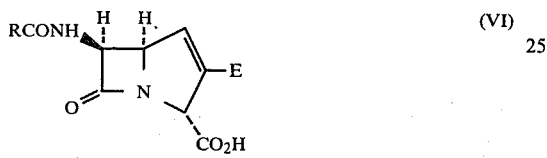    (VI)

and pharmaceutically acceptable salts and in vivo hydrolysable esters thereof wherein R and E are as defined in relation to a compound of the formula (II). This depicted optical isomer has the configuration 2R, 5R, 6S.

In another aspect of this invention there is provided a pharmaceutical composition which comprises a compound of the formula (II) or a pharmaceutically acceptable salt or in vivo hydrolysable ester thereof as hereinbefore defined and a pharmaceutically acceptable carrier.

Such compositions are normally provided in unit dose form containing from 50 to 500 mg or more usually from 100 to 250 mg of a compound of this invention.

The compositions of this invention are usually adapted for administration to animals including humans. Such compositions may be formulated in a conventional manner for antibacterial agents, for example in a similar manner to that known from penicillins and cephalosporins.

The compounds of this invention may be provided in orally administrable form, for example as tablets or capsules. The compounds of this invention may be provided in a form suitable for administration by injection or infusion, for example in the form of a sterile salt such as the sterile sodium salt sealed in a vial ampoule.

It is believed that infections most readily treated by the compounds of this invention are those due to strains of Bacillus, Staphylococcus and Streptococcus.

The present invention also provides a process for the preparation of a compound of the formula (II) or its pharmaceutically acceptable salt or in vivo hydrolysable ester as hereinbefore defined which process comprises the ring-closing elimination of O=$PY_1Y_2Y_3$ from a hydrogenolysable ester of a compound of the formula (VII):

wherein G is an azido group or a group RCONH wherein R and E are as defined in relation to a compound of the formula (II) and $Y_1$, $Y_2$ and $Y_3$ are independently selected from phenyl or optionally substituted phenyl; and thereafter if G is an azido group, reducing it to an amino group and subsequently acylating said amino group or derivative thereof with an N-acylating derivative of a carboxylic acid of the formula (VII a):

    (VII a)

wherein R is the hereinabove defined and any group capable of being acylated is optionally protected:

and thereafter if necessary:

(a) hydrogenating the hydrogenolysable ester to provide a free acid or salt of the compound of the formula (II):

(b) re-esterifying such a free acid or salt to form an in-vivo hydrolysable ester.

Preferably in the above reaction G is a group RCONH.

The term "acylating derivative of a carboxylic acid" includes any N-acylating compound suitable for the performance of analogous reactions with 6-aminopenicillanic acid or 7-aminocephalosporanic acid or salts or esters thereof, for example an acid halide, a mixed anhydride or other reactive derivative such as that produced by the reaction of an acid with an enzyme or a condensation-promoting agent such as dicyclohexylcarbodi-imide or its chemical equivalent. Reactive groups present in such acylating agents may be protected in conventional manner.

Such N-acylating compounds may be summarised by the formula (VII b):

    (VII b)

wherein R is as defined in relation to a compound of the formula (II) and W is a readily displaceable group. Most suitably W is a bromine atom. Preferably W is a chlorine atom.

Reduction of the azido group to an amino group may be performed in conventional manner.

Suitably the ester of the compound of the formula (VII) is prepared by the reaction of a hydrogenolysable ester of a compound of the formula (VIII):

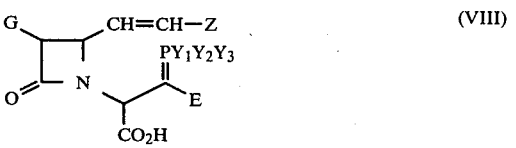    (VIII)

wherein G, E, $Y_1$, $Y_2$ and $Y_3$ are as defined in relation to a compound of the formula (VII), and Z is an inert organic group; with ozone, Suitably this reaction is performed in the presence of an acid. It is convenient to carry out the transformation of the ester of the compound of the formula (VIII) to the ester of the compound of the formula (II) without isolation of the intermediate ester of the aldehyde of the formula (VII).

Suitable groups R and E for use in the foregoing processes are as defined in relation to compounds of the formulae (II)–(V).

Suitable groups $Y_1$, $Y_2$ and $Y_3$ include phenyl and phenyl substituted by a lower alkoxy or lower alkyl group.

More suitably $Y_1$, $Y_2$ and $Y_3$ are selected from phenyl, methoxyphenyl or methylphenyl.

A preferred value for each of $Y_1$, $Y_2$ and $Y_3$ is the phenyl group.

Suitable groups Z include $C_{1-6}$ alkyl optionally substituted by $C_{1-3}$ alkoxy, $C_{1-3}$ acyloxy, $C_{1-3}$ alkoxycarbonyl, phenyl optionally substituted by any of the above; and $C_{1-6}$ alkoxycarbonyl.

More suitably Z is a methyl, ethyl, propyl, butyl, phenyl, methoxyphenyl, ethoxyphenyl, methylphenyl, ethylphenyl, methoxycarbonylmethyl, methoxycarbonylethyl, acetoxymethyl, acetoxyethyl, methoxycarbonyl or ethoxycarbonyl group.

Preferably Z is a phenyl group.

Preferably Z is a methoxycarbonyl group.

Any group R that contains a reactive moiety such as $NH_2$ or $CO_2H$ may be suitably protected during the foregoing process and during the hereinafter defined processes. For example an amino group may be reacted with a p-nitrobenzyloxycarbonyl halide to give a p-nitrobenzyloxycarbonylamino moiety which is cleavable on hydrogenation to yield the amino moiety. Similarly a hydrogenolysable ester may be formed in conventional manner from a $CO_2H$ moiety which moiety may be reformed on hydrogenation.

Suitably the preparation of a hydrogenolysable ester of a compound of the formula (II) is performed in an organic solvent, for example in chloroform, ethyl acetate, dichloromethane, dichloroethane or in mixtures thereof.

We have found it most convenient to use a mixture of ethyl acetate and dichloromethane.

The process is normally carried out at a depressed temperature, for example $-80°$ to $20°$ C., more usually at about $-70°$ to $-50°$ C. In general ozone is passed through the solution until a light blue colour is produced. At this point excess ozone is removed by flushing with an inert gas. The intermediate ozonide may now be reduced by the addition of a conventional reducing agent.

The process is suitably carried out in the presence of trifluoroacetic acid.

The reaction mixture is then neutralised and the desired compound isolated by conventional means, for example by crystallisation, chromatography or countercurrent separation. We have found it most convenient to use a combination of chromatography and crystallisation.

The hydrogenolysable ester of a compound of the formula (II) is cleaved by catalytic hydrogenation. Particularly suitable esters for use in this process include benzyl esters, optionally substituted in the para position by a lower alkoxy, or nitro group or halogen atom.

A preferred ester for use in this process is the p-nitrobenzyl ester.

Suitable methods include hydrogenation in the presence of a transition metal catalyst. The pressure of hydrogen used in the reaction may be low, medium or high but in general an approximately atmospheric or slightly super-atmospheric pressure of hydrogen is preferred. The transition metal catalyst employed is preferably palladium on charcoal or on calcium carbonate. The hydrogenation may be effected in any inert solvent in which the ester is soluble such as aqueous dioxan or the like. If this hydrogenation is carried out in the presence of a base then a salts of compounds (II) is produced. Suitable bases for inclusion include $NaHCO_3$, $KHCO_3$, $Na_2CO_3$, $K_2CO_3$, $CaCO_3$, $MgCO_3$, $LiHCO_3$, $NH_4OCOCH_3$ and the like. If no base is present then hydrogenation leads to the preparation of an acid within formula (II) which may then be neutralised if desired to yield a salt. Suitable bases which may be used to neutralise acids within formula (II) include LiOH, NaOH, $NaHCO_3$, KOH, $Ca(OH)_2$ and $Ba(OH)_2$.

The salts of acids of the formula (II) may be converted to esters in conventional manner. Suitable methods include the reaction of an alkali metal salt such as a sodium or potassium salt with a reactive halide or sulphonate ester such as a bromide, chloride, mesylate or tosylate, for example bromophthalide. Such esterifications may be carried out under conventional conditions, for example in dimethylformamide at room temperature.

In a further aspect the present invention provides a process for the preparation of a hydrogenolysable ester of a compound of the formula (VIII) which process comprises the reaction of a corresponding ester of a compound of the formula (IX):

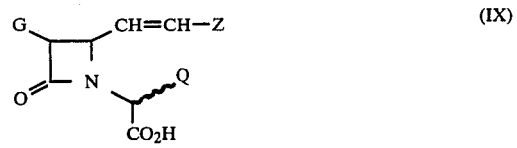
(IX)

wherein G and Z are as defined in relation to formula (VIII) and Q is a chlorine or bromine atom, with a compound of the formula (X):

$Y_1Y_2Y_3P=CH-E$ (X)

wherein $Y_1, Y_2, Y_3$ and E are as defined in relation to formula (VII).

The reaction is suitably performed in an inert organic solvent for example dichloromethane or chloroform. It is preferred that the solvent used be anhydrous, and that the reaction be conducted in an inert atmosphere such as argon.

Suitably the reaction is carried out at a nonextreme temperature for example $-30°$ C. to $+70°$ C., more suitably $0°$ C. to $40°$ C. and conveniently at ambient.

The product can be isolated in conventional manner.

A hydrogenolysable ester of a compound of the formula (IX) may be prepared by the reaction of a corresponding ester of a compound of the formula (XI):

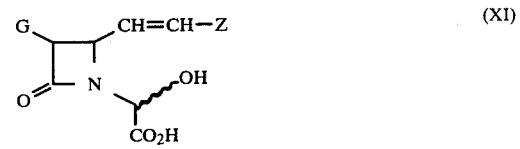
(XI)

wherein G and Z are as defined in relation to formula (VIII) with thionyl bromide or thionyl chloride.

This reaction is also normally effected in the presence of at least one equivalent of a base of relatively low nucleophilicity in a dry solvent such as dioxan or tetrahydrofuran at a depressed temperature for example −30° C. to −10° C.

A hydrogenolysable ester of a compound of the formula (XI) may be prepared by the reaction of a compound of the formula (XII):

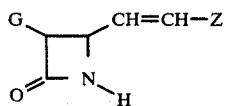
(XII)

wherein G and Z are as defined in relation to formula (VIII) with a glyoxylic acid ester.

Normally this reaction is carried out in an inert solvent at an elevated temperature, for example in dry benzene under reflux.

A compound of the formula (XII) wherein G is RCONH and Z is restricted to the value of E as defined in relation to formula (II) may be prepared by the consecutive treatment of an ester of a compound of the formula (XIII):

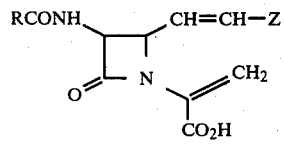
(XIII)

wherein R and Z are as defined in relation to formula (VIII), with ozone, a tri-aryl phosphine and a compound of the formula (X):

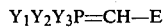
$Y_1Y_2Y_3P=CH-E$ (X)

wherein $Y_1$, $Y_2$, $Y_3$ and E are as defined in relation to formula (VII).

An ester of a compound of the formula (XIII) may be prepared from a corresponding ester of a compound of the formula (XIV):

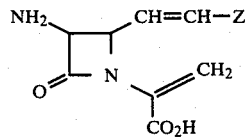
(XIV)

wherein Z is as defined in relation to formula (VIII), by conventional chemical methods of acylation known to those skilled in the art of penicillin and cephalosporin chemistry.

An ester of a compound of the formula (XIV) may be prepared from a corresponding ester of a compound of the formula (XV):

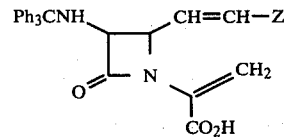
(XV)

wherein Z is as defined in relation to formula (VIII), by treatment with an acidic catalyst such as p-toluenesulphonic acid, in conventional manner well known to those skilled in the art of penicillin and cephalosporin chemistry.

An ester of a compound of the formula (XV) may be prepared by the reaction of a corresponding ester of a compound of the formula (XVI):

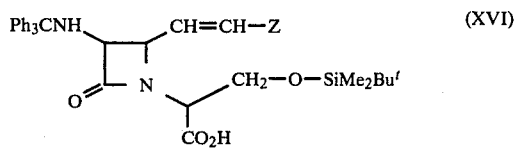
(XVI)

wherein Z is as defined in relation to formula (VIII), with tetraethylammonium fluoride in tetrahydrofuran at ambient temperature.

An ester of a compound of the formula (XVI) may be prepared by the reduction of a corresponding ester of a compound of the formula (XVII):

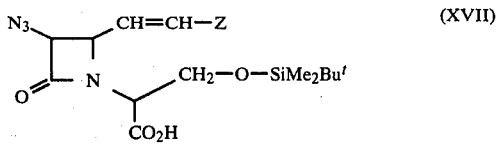
(XVII)

wherein Z is as defined in relation to formula (VII), with hydrogen sulphide, followed by alkylation of the resultant amino group with triphenylmethylchloride.

Esters of the compound of the formula (XVII) are prepared by the procedures disclosed in Canadian Journal of Chemistry Vol. 56, page 211 (1978) G. Just and T-J. Liak.

Alternatively esters of the compound of the formula (XI) may be prepared by the methods summarised in the accompanying flow-sheet (Scheme I) which may be read in conjunction with the Examples contained herein.

Scheme I

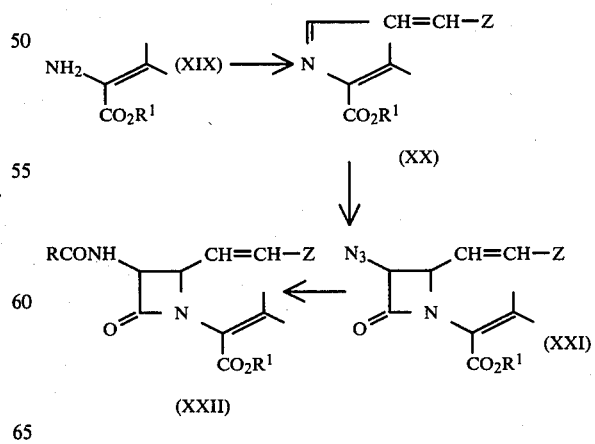

-continued
Scheme I

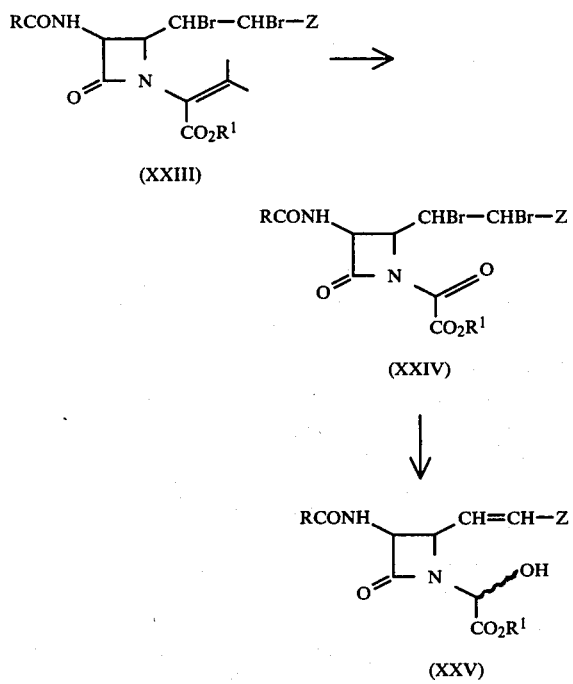

$R^1$ is an esterifying radical

Compounds of the formula (XII) wherein Z is restricted to the value of E may be prepared by the methods summarised in the following flow-sheets (Scheme 2 and Scheme 3) which may be read in conjunction with the accompanying Examples contained herein.

Scheme 2

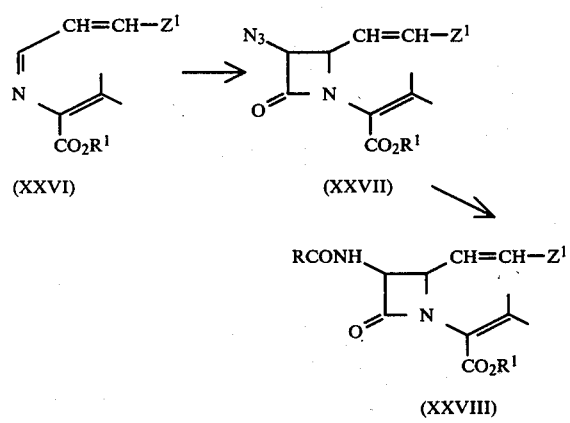

-continued
Scheme 2

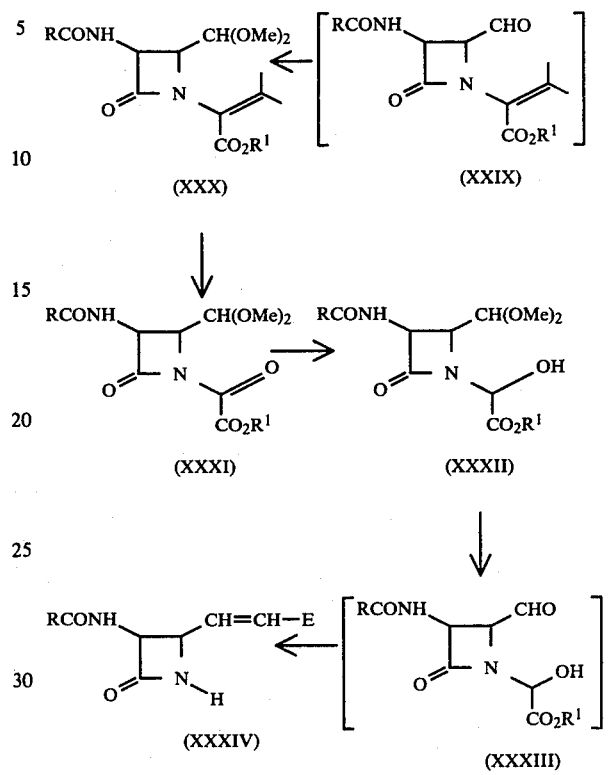

$R^1$ = esterifying radical
$Z^1$ = inert organic group

Scheme 3

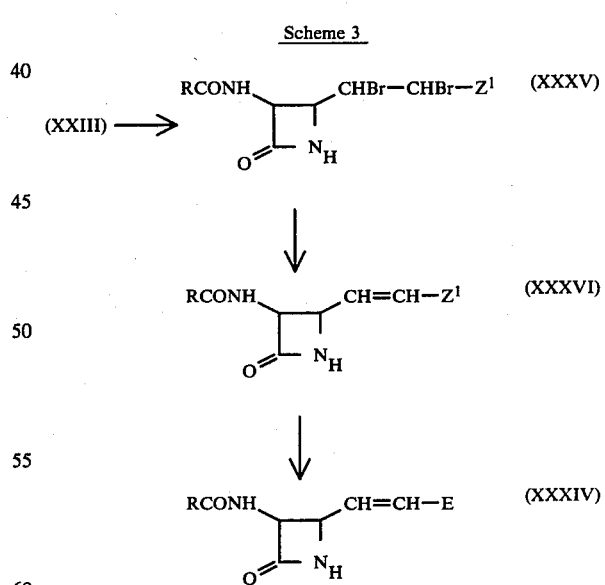

$R^1$ = esterifying radical
$Z^1$ = inert organic group

In addition the compound of the formula (XXXVI) may be prepared by the methods of Scheme 4 which should be read in conjunction with Examples 40–43; the essence of this general route being the oxidative removal of the p-methoxymethoxyphenyl protecting group using ceric ammonium nitrate in aqueous tetrahydrofuran.

Scheme 4

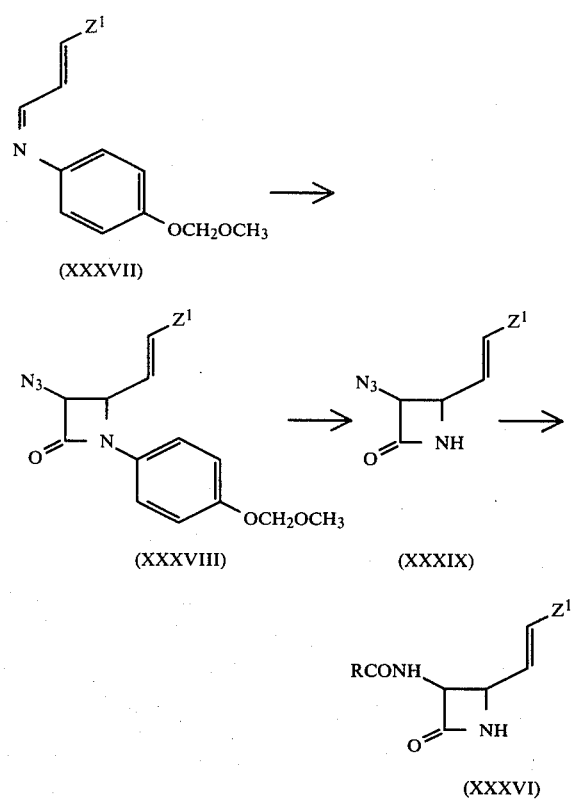

$Z^1$ = inert organic group

Compounds of the formulae (VII), (VIII), (IX) and (XII) are novel and as such form part of this invention.

The processes of this invention are illustrated by the following Examples.

EXAMPLE 1

Methyl 2-amino-(N-cinnamylidene)-3,3-dimethyl acrylate (2)

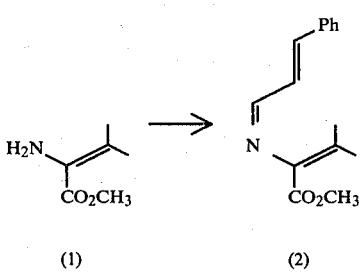

Methyl 2-amino-3,3-dimethyl acrylate (1; A. G. Brown and T. C. Smale, J. Chem. Soc. Perkin 1, 65, 1972; 4.75 g) in dry methylene dichloride (35 ml) was vigorously stirred with trans-cinnamaldehyde (4.86 g) and anhydrous magnesium sulphate (2 g) at ambient temperature for 17 h. The mixture was filtered, evaporated, and dried in vacuo to give the Schiff base (2) as a dark orange gum (8.94 g). $\nu_{max.}$ (CHCl$_3$) 1720, 1678, 1625 cm$^{-1}$; δ ppm (CDCl$_3$) 1.96 (3H, s), 2.02 (3H, s), 3.83 (3H, s), 7.00 (1H, d), 7.2–7.7 (6H, m), 7.90 (1H, t).

EXAMPLE 2 cis 3-Azido-1-(1-methoxycarbonyl-2-methylprop-1-enyl)-4-styryl-azetidin-2-one (3)

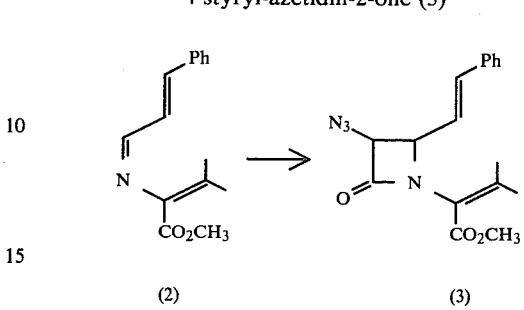

Azidoacetic acid (5.58 g) was dissolved in dry methylene dichloride (50 ml) at 0° under argon trifluoroacetic anhydride (7.78 ml) added dropwise over 10 min. After 15 min, triethylamine (7.64 ml) in methylene dichloride (5 ml) was carefully added dropwise, over 15 min., and stirring at 0° continued a further 45 min. The solution was transferred under argon to a dropping funnel, cooled to −76°, and added over 1 h to a mixture of the Schiff base (2) (8.94 g) and triethylamine (7.64 ml) in methylene dichloride (80 ml) at 0°. After a further 1 h at 0° the solution was diluted with methylene dichloride, washed successively with water, dilute aqueous sodium hydrogencarbonate, brine, dried (MgSO$_4$) and evaporated. Chromatography of the residue on silica H afforded the product (3; 7.17 g) as a dark orange oil. $\lambda_{max.}$ (EtOH) 256 nm ($\epsilon$ 23,000); $\nu_{max.}$ (CHCl$_3$) 2120, 1762, 1723, 1650, 1633 cm$^{-1}$; δ ppm (CDCl$_3$) 1.95 (3H, s), 2.16 (3H, s), 3.71 (3H, s), 4.69 (1H, dd, J 5 and 8 Hz), 4.83 (1H, d, J 5 Hz), 6.13 (1H, dd, J 8 and 16 Hz), 6.60 (1H, d, J 16 Hz), 7.1–7.4 (5H, m). (Found: C, 62.4; H, 5.6; N, 17.5. C$_{17}$H$_{18}$N$_4$O$_3$ requires C, 62.6; H, 5.5; N, 17.2%).

EXAMPLE 3 cis 1-(1-Methoxycarbonyl-2-methylprop-1-enyl)-3-phenoxyacetamido-4-styryl-azetidin-2-one (5)

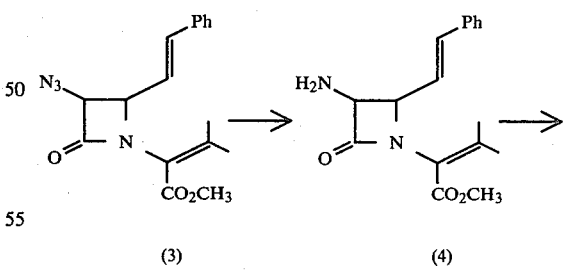

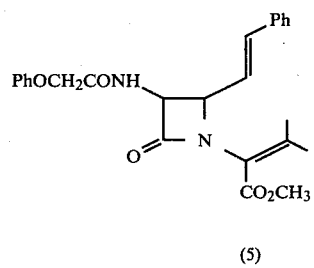

To the β-lactam (3; 3.51 g) in dry methylene dichloride (100 ml) at 0° was added triethylamine (1.63 ml). Hydrogen sulphide was bubbled through the mixture for 5 min. and the resulting dark solution stood at 0° for 1.5 h. The solvent was then removed under reduced pressure and the residue re-evaporated (×3) from methylene dichloride, to afford the crude amine (4) as an orange solid. Without further purification, the β-lactam (4) was dissolved in dry methylene dichloride (50 ml) at −20° and triethylamine (1.63 ml) added, followed by dropwise addition of phenoxyacetyl chloride (1.63 ml) in methylene dichloride (5 ml) over 10 min. The solvent was evaporated and the residue taken up in ethyl acetate, washed successively with water, dilute aqueous sodium hydrogencarbonate, brine, dried (MgSO$_4$) and evaporated to a gum. Chromatography on silica H provided the product (5; 3.62 g) as an amorphous solid. λ$_{max}$. (EtOH) 258 nm (ε$_m$22,300); ν$_{max}$. (CHCl$_3$) 3420, 1755, 1720, 1685, 1650 sh, 1630 sh cm$^{-1}$; δ ppm (CDCl$_3$) 2.03 (3H, s), 2.16 (3H, s), 3.69 (3H, s), 4.42 (2H, s), 4.71 (1H, dd, J 5 and 8 Hz), 5.29 (1H, dd, J 5 and 8 Hz), 6.07 (1H, dd, J 8 and 16 Hz), 6.53 (1H, dd, J 8 and 16 Hz), 6.6–7.3 (10H, m), 7.35 (1H, d, J 8 Hz). (Found: C, 69.2; H, 6.3; N, 6.4. C$_{25}$H$_{26}$N$_2$O$_5$ requires C, 69.1; H, 6.0; N, 6.5%).

EXAMPLE 4 cis 4-(1,2-Dibromo-2-phenyl ethyl)-1-(1-methoxycarbonyl-2-methylprop-1-enyl)-3-phenoxyacetamido-azetidin-2-one (6)

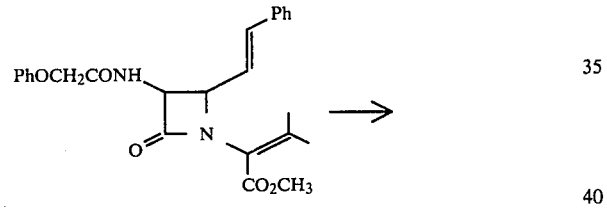

(5)

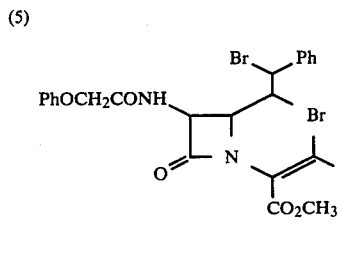

(6)

The β-lactam (5; 3.62 g) was dissolved in dry methylene dichloride (70 ml) at 0° and bromine (0.48 ml) in methylene dichloride (10 ml) added dropwise over 15 min. After an additional 10 min. the reaction mixture was concentrated (15 ml) and poured onto a column of silica H. Chromatography afforded the dibromide (6; 2.8 g) (2:1 mixture of isomers A and B) as an amorphous solid. λ$_{max}$. (EtOH) 244 nm (ε$_m$ 9550); ν$_{max}$. (CHCl$_3$) 3420, 1765, 1720, 1690, 1630 cm$^{-1}$; δ ppm (CDCl$_3$) 1.97 (3H, s, isomer A), 2.17 (3H, s, isomer A), 2.22 (6H, s, isomer B), 3.78 (3H, s), 4.51 (1H, d, J 11 Hz, isomer A), 4.53 (2H, s), 4.71 (1H, d, J 11 Hz, isomer B), 4.95 (1H, m, isomer A), 5.14 (1H, d, J 6 Hz, each part showing some further coupling, isomer B), 5.7 (1H, m), 6.8–7.5 (11H, m), 7.65 (1H, d, J 11 Hz). (F.D. spectra show M$^+$ at 596, 594, 592 (correct isotope ratios) and fragmentation peaks at m/e 514,512 [M-HBr]).

EXAMPLE 5 cis 1-(1-Hydroxy-1-methoxycarbonylmethyl)-3-phenoxyacetamido-4-styryl-azetidin-2-one (8)

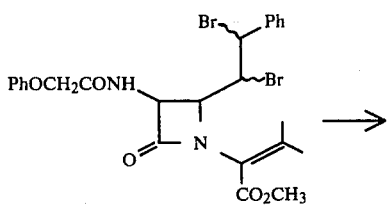

(6)

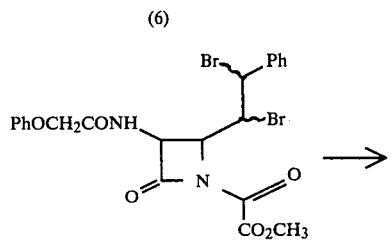

(7)

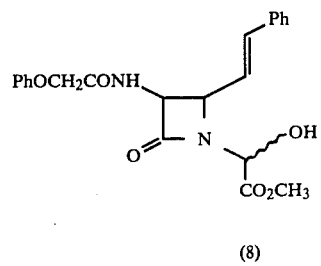

(8)

Ozonised oxygen was bubbled through a solution of the β-lactam (6; 1.7 g) in dry methylene dichloride (35 ml) at −20° for 1 hour. Dry argon was bubbled through the solution for 20 min, followed by the addition of dimethyl sulphide (2.04 ml). After 30 min the reaction mixture was allowed to reach ambient temperature and glacial acetic acid (3 drops) added. The mixture was diluted with ethyl acetate (150 ml), and washed successively with water (×2), brine, dried (MgSO$_4$) and evaporated to afford the dibromo-oxamide (7; 1.7 g) as an amorphous solid ν$_{max}$. (CHCl$_3$) 3400, 1820, 1760, 1710, 1690 cm$^{-1}$.

Without further purification, activated zinc dust (2.43 g) was added portionwise over a few minutes, with occasional cooling, to the β-lactam (7: 1.7 g) in dry methylene dichloride (10 ml) and glacial acetic acid (10 ml) at room temperature. After 30 min the mixture was filtered through kieselguhr, and the filter cake washed copiously with ethyl acetate. The filtrate was washed successively with water (×3), dilute aqueous sodium hydrogencarbonate, brine, dried (MgSO$_4$) and evaporated to give a white solid (1.2 g). Chromatography on silica H afforded the product (8; 0.56 g) as a mixture of isomers (1:1) m.p. 142°–143° (ethyl acetate-light petroleum 60°–80°); λ$_{max}$. (EtOH) 258 nm (ε17,000); ν$_{max}$. (CHCl$_3$) 3400, 3300b, 1765, 1750, 1685 cm$^{-1}$; δ ppm (CDCl$_3$) 3.60 (3H,s, isomer 1), 3.82 (3H, s, isomer 2), 4.37 (2H, s), 4.66 (2H, m, collapses to 1H, dd, J8 and 5 Hz on exch.), 5.42 (1H, dd, J8 and 9 Hz, isomer 2), 6.11 (1H, dd, J8 and 16 Hz, isomer 1), 6.5–7.3 (11H, m), 7.45 (1H, d, J 9 Hz). (Found: C, 64.2; H, 5.5; N,6.9; $C_{22}H_{22}N_2O_6$ requires C, 64.4; H, 5.4; N, 6.8%).

EXAMPLE 6 cis 1-[1,2-Dimethoxycarbonyl-2-triphenylphosphoranylidene-ethyl]-3-phenoxyacetamido 4-styryl-azetidin-2-one (10)

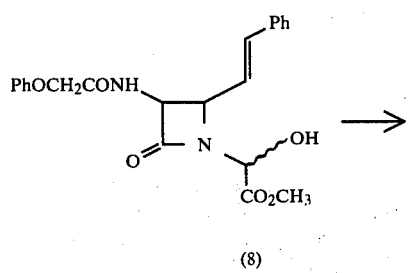

(8)

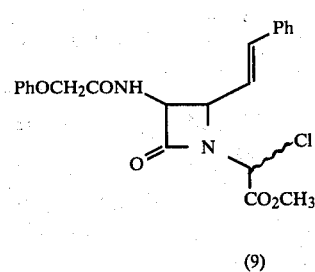

(9)

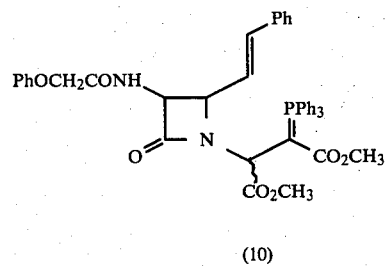

(10)

The hydroxy-compound (8; 362 mg) was dissolved in dry tetrahydrofuran (10 ml) and cooled to −20° under argon. 2,6-Lutidine (147 mg) was added, followed by dropwise addition of thionyl chloride (160 mg) in dry tetrahydrofuran (2 ml) over 10 min. After 5 min. the mixture was rapidly filtered under argon and the filtrate was evaporated and dried in vacuo for 15 min to give (9) as a gum. $\nu_{max}$. (CHCl₃) 3400, 1790, 1760, 1685, 1650 cm⁻¹.

The total crude product (9) was dissolved in dry methylene dichloride (10 ml) containing carbomethoxymethylenetriphenylphosphorane (648 mg). The solution was left at ambient temperature under argon for 24 hours, then evaporated and the residue chromatographed on silica H to give the product (10; 388 mg) as an inseparable mixture of isomers, m.p. 175–178 (dc) (ethylacetate-light petroleum 60°–80°) $\nu_{max}$. (CHCl₃) 3425, 1750, 1740 sh, 1690, 1620 cm⁻¹. (Found: C, 70.6; H, 5.3; N, 4.1; $C_{43}H_{39}N_2O_7P$ requires C, 71.1; H, 5.4; N, 3.9%).

EXAMPLE 7

(2RS, 5RS, 6SR) Methyl 1-Aza-3-methoxycarbonyl-6-phenoxyacetamido-bicyclo[3.2.0]-hept-3-en-7-one-2-carboxylate (11)

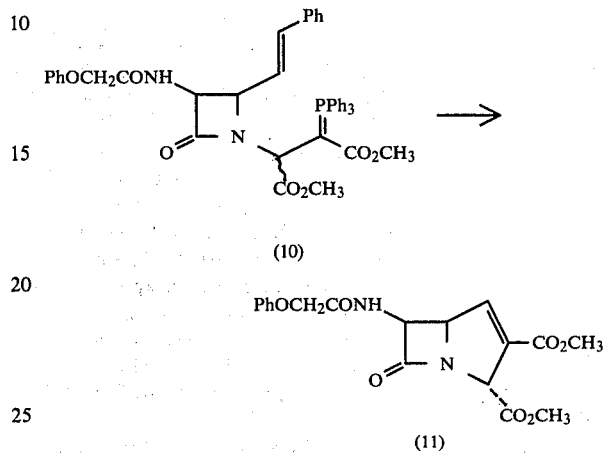

Trifluoroacetic acid (0.21 ml) was added to the β-lactam (10; 0.2 g) in ethyl acetate (8 ml) and methylene dichloride (2 ml), and after 10 min. the solution was cooled to −76° and ozonised oxygen bubbled through until a pale blue colour persisted. Argon was passed through the solution for 20 min. followed by the addition of triphenylphosphine (0.073 g) in ethyl acetate (1 ml), pre-cooled to −76°. After 20 min. the reaction mixture was transferred to an icebath and carefully neutralised with saturated sodium hydrogencarbonate solution. The organic phase was separated, washed with brine (×3), dried (MgSO₄) and evaporated to an oil. Chromatography on silica H provided the product (11: 0.05 g) as a white crystalline solid m.p. 82°–85° (ethyl acetate-light petroleum 60°–80°), $\lambda_{max}$. (EtOH) 270 ($\epsilon_m$ 1750) 277 n.m. (1300). $\nu_{max}$. (Nujol) 3360, 1790, 1740, 1730, 1690, 1660, 1620 cm⁻¹; δ ppm (CDCl₃) 3.76 (3H, s), 3.79 (3H, s), 4.54 (2H, s), 5.01 (1H, m, J 5.3, 3.5 and 1.8 Hz), 5.36 (1H, dd, J 2.4 and 1.8 Hz), 5.56 (1H, dd, J 7.2 and 5.3 Hz), 7.10–7.42 (7H, m). (Found: C, 57.8; H, 4.6; N, 7.6; $C_{18}H_{18}N_2O_7$ requires C, 57.8; H, 4.8; N, 7.5%).

EXAMPLE 8

Benzyl 3,3-Dimethyl-2-nitroacrylate (13)

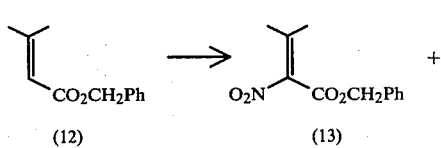

(12)    (13)

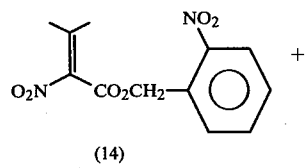

(14)

-continued

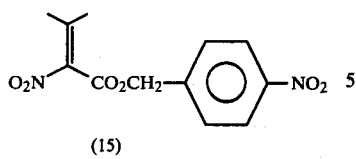

Benzyl 3,3-dimethylacrylate (80 g) was added dropwise to a well stirred mixture of fuming nitric acid (157 ml. 95%) and water (34 ml) at −20° over 1 h, (cf. A. G. Brown and T. C. Smale, J. Chem. Soc. Perkin 1, 65, 1972). After 2 h at −20° and warming of 0° for 2 h, the reaction mixture was poured into ice (800 ml) and extracted with chloroform (3×200 ml). The combined organic extracts were washed successively with water (3×200 ml), saturated sodium hydrogencarbonate solution (2×350 ml), brine (2×200 ml), dried (MgSO$_4$) and evaporated to an oily residue. Chromatography on silica H gave the product (13; 36 g) as an oil. $\nu_{max}$. (film) 1715, 1650, 1530, 1370 cm$^{-1}$; δ ppm (CDCl$_3$) 1.98 (3H, s), 2.23 (3H, s), 5.20 (2H, s), 7.40 (5H, m). (Found: C, 61.2; H, 5.7; N, 6.0; C$_{12}$H$_{13}$NO$_4$ requires C, 61.3; H, 5.5; N, 6.0%).

Further elution of the column provided the o-nitrobenzyl 2-nitro-3,3-dimethyl acrylate (14), and p-nitrobenzyl 2-nitro-3,3-dimethyl acrylate (15) as white solids (47 g). Ortho isomer (14) $\nu_{max}$. (CHCl$_3$) 1735, 1650, 1530, 1350 cm$^{-1}$; δ ppm (CDCl$_3$) 2.03 (3H, s), 2.30 (3H, s), 5.73 (2H, s), 7.4–7.8 (4H, m), para isomer (15) $\nu_{max}$. (CHCl$_3$) 1735, 1650, 1530, 1350 cm$^{-1}$; δ ppm (CDCl$_3$) 2.03 (3H, s), 2.30 (3H, s), 5.36 (2H, s), 7.52 and 8.30 (4H, ABq, J 9 Hz).

EXAMPLE 9

Benzyl 2-Amino-(N-cinnamylidene)-3,3-dimethyl acrylate (17)

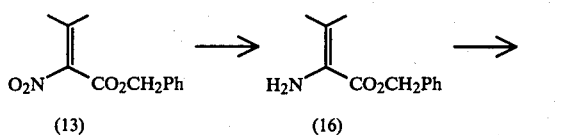

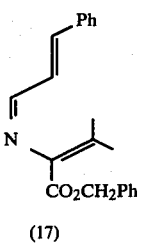

Benzyl 3,3-dimethyl-2-nitroacrylate (13; 17.2 g) was converted to benzyl 2-amino-3,3-dimethylacrylate (16; 12.2 g) using the same conditions as for the corresponding methyl ester (A. G. Brown and T. C. Smale, J. Chem. Soc. Perkin I, 65, 1972). $\nu_{max}$. (CHCl$_3$) 1710, 1690, 1640 cm$^{-1}$; δ ppm (CDCl$_3$) 1.70 (3H, s), 2.05 (3H, s), 2.8–3.7 (2H, m, exch.), 5.17 (2H, s), 7.31 (5H, s). The crude product (16; 80% pure by t.l.c. and n.m.r.) was reacted with trans-cinnamaldehyde (7.72 g) and anhydrous magnesium sulphate (7 g) as described in Example 1 to give the Schiff base (17) as a red gum (19.7 g). $\lambda_{max}$. (EtOH) 297 nm (ε 27,600) $\nu_{max}$. (CHCl$_3$) 1710, 1675, 1625 cm$^{-1}$; δ ppm (CDCl$_3$) 1.91 (3H, s), 2.00 (3H, s), 5.26 (2H, s), 6.5–7.6 (7H, m), 7.75 (1H, d, J 7 Hz).

EXAMPLE 10 cis 3-Azido-1-(1-benzyloxycarbonyl-2-methylprop-1-enyl)-4-styryl-azetidin-2-one (18)

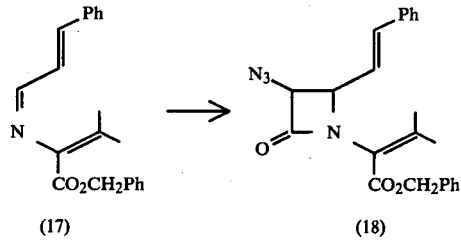

The Schiff base (17; 19.7 g) was converted into (18; 12.6 g) as described in Example 2. The product was isolated as a pale red-orange gum. $\lambda_{max}$. (EtOH) 256 n.m. (ε 23,400) $\nu_{max}$. (CHCl$_3$) 2115, 1760, 1720 cm$^{-1}$; δ ppm (CDCl$_3$) 1.98 (3H, s), 2.21 (3H, s), 4.63 (1H, dd, J 7 and 10 Hz), 4.79 (1H, d, J 7 Hz), 5.08 and 5.32 (2H, ABq, J 15 Hz), 6.11 (1H, dd, J 10 and 20 Hz), 6.48 (1H, d, J 20 Hz), 7.29 (5H, s), 7.37 (5H, s). (Found: C, 68.4; H, 5.5; N, 14.0; C$_{23}$H$_{22}$N$_4$O$_3$ requires C, 68.7; H, 5.5; N, 13.9%).

EXAMPLE 11 cis 1-(1-Benzyloxycarbonyl-2-methylprop-1-enyl)-3-phenoxyacetamido-4-styrylazetidin-2-one (20)

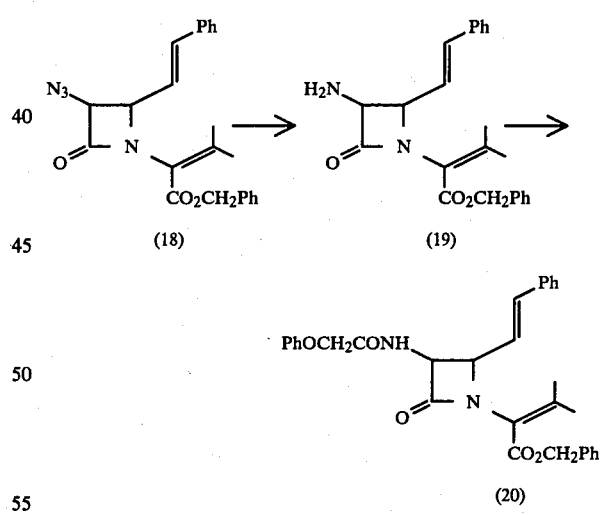

The azido-lactam (18; 6.38 g) was reduced and acylated as described in Example 3 to provide the acylamino derivative (20; 5.5 g) as a white crystalline solid, m.p. 107°–108° (ethyl acetate-light petroleum 60°–80°). $\lambda_{max}$. (EtOH) 258 nm (23,200); $\nu_{max}$. (CHCl$_3$) 3245, 1755, 1690, 1650 sh, 1630 sh, cm$^{-1}$; δ ppm (CDCl$_3$) 2.05 (3H, s), 2.18 (3H, s), 4.44 (2H, s), 4.67 (1H, dd, J 5 and 8 Hz), 5.08 and 5.27 (2H, ABq, J 12 Hz), 5.20 (1H, dd, J 5 and 8 Hz), 6.04 (1H, dd, J 8 and 16 Hz), 6.47 (1H, d, J 16 Hz), 6.7–7.5 (10H, m), 7.63 (1H, d, J 8 Hz, exch.). (Found: C, 72.7; H, 5.9; N, 5.4; C$_{31}$H$_{30}$N$_2$O$_5$ requires C, 72.9; H, 5.9; N, 5.5%).

EXAMPLE 12 cis 1-(1-Benzyloxycarbonyl-2-methylprop-1-enyl)-4-(1,1-dimethoxymethyl)-3-phenoxyacetamido-azetidin-2-one (22)

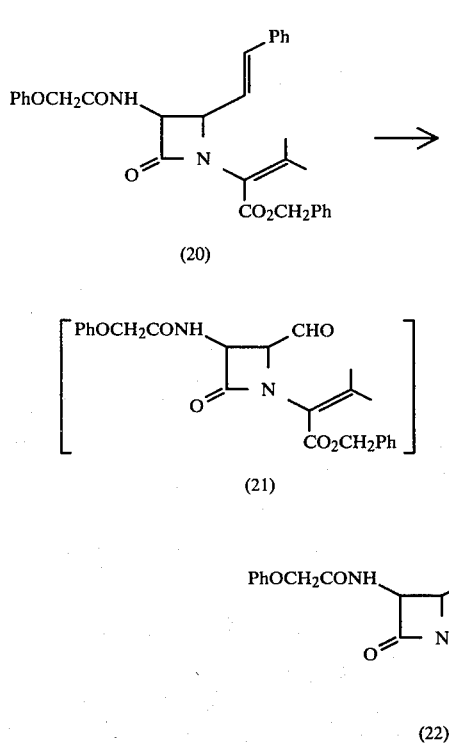

Ozonised oxygen was bubbled through a solution of the β-lactam (20; 3.06 g) in methylene dichloride (30 ml) at −76° for 1.5 h when cleavage of the 4-styryl moiety was complete. Argon was then bubbled through the solution for 20 min followed by the addition of triphenylphosphine (1.56 g) in a little methylene dichloride, and the reaction allowed to reach ambient temperature. After 1.5 h the solvent was removed and the residual aldehyde (21) immediately taken up in methanol (50 ml) and 2,2-dimethoxypropane (20 ml). The solution was refluxed for 16 h in the presence of p-toluene sulphonic acid as catalyst. The reaction mixture was diluted with ethyl acetate, washed with dilute aqueous sodium hydrogencarbonate, brine, dried (MgSO$_4$) and evaporated to a residual oil. Chromatography on silica H provided the product (22; 2.6 g) $\nu_{max}$. (CHCl$_3$) 3420, 1755, 1715 sh, 1685, 1630 cm$^{-1}$; δ ppm (CDCl$_3$) 2.02 (3H, s), 2.20 (3H, s), 3.22 (6H, s), 4.17 (1H, dd, J 3 and 6 Hz), 4.33 (1H, d, J 3 Hz), 4.60 (2H, s), 5.08 and 5.30 (2H, ABq, J 12 Hz)., 5.47 (1H, dd, J 6 and 10 Hz), 6.8–7.5 (10H, m), 7.6 (1H, d, J 10 Hz). (Found: C, 64.7; H, 6.2; N, 5.8; C$_{26}$H$_{30}$N$_2$O$_7$ requires C, 64.7; H, 6.2; N, 5.8%).

EXAMPLE 13 cis 4-(1,1-Dimethoxymethyl)-1-(1-hydroxy-1-benzyloxycarbonylmethyl)-3-phenoxyacetamido-azetidin-2-one (23)

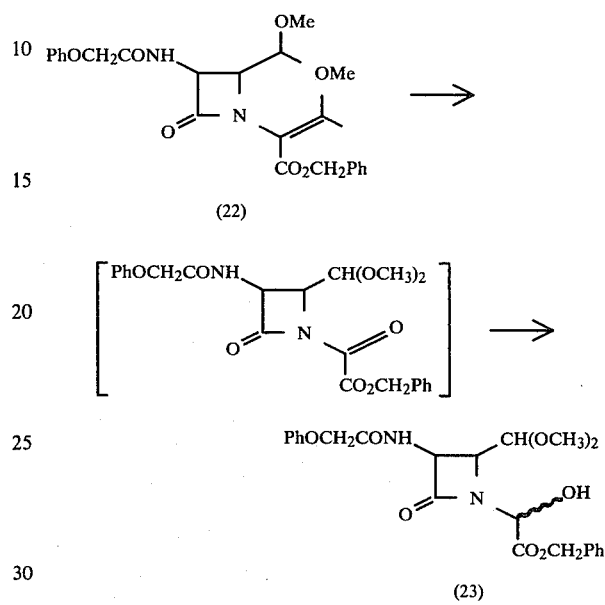

Ozonised oxygen was bubbled through the β-lactam (22; 2.4 g) in dry methylene dichloride (20 ml) at −20° for 30 min. Argon was then bubbled through the solution for 10 min. which was then equilibrated with ambient temperature over 45 min. Glacial acetic acid (15 ml) was added, followed by activated zinc dust (3.6 g) portionwise with occasional cooling over 10 min. After 2 h at room temperature the mixture was filtered, diluted with ethyl acetate, and washed successively with water (×3), saturated aqueous sodium hydrogencarbonate (×2), brine, dried (MgSO$_4$) and evaporated. Chromatography on silica H afforded the glycolate (23) as a mixture of separable isomers (1.9 g). $\nu_{max}$. (CHCl$_3$) 3500–3300 b, 3420, 1775, 1760, 1685 cm$^{-1}$; δ ppm (CDCl$_3$) 3.23 and 3.31 (3H, s), 3.87 (1H, dd, J 3 and 6 Hz), 4.34 (1H, d, J 3 Hz), 4.52 (2H, s), 5.25 (2H, s), 5.48 and 5.63 (1H, s), 5.53 (1H, dd, J 6 and 10 Hz), 6.8–7.6 (10H, m), 7.65 (1H, d, J 10 Hz). (Found: C, 60.3; H, 6.0; N, 6.1; C$_{23}$H$_{26}$N$_2$O$_8$ requires C, 60.3; H, 5.7; N, 6.1%).

EXAMPLE 14 cis 4-(2-Methoxycarbonylvinyl)-3-phenoxyacetamido-azetidin-2-one (25)

Method A

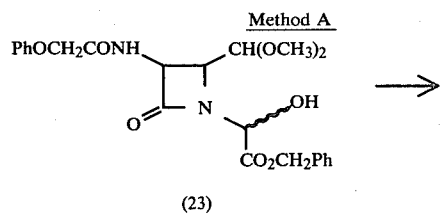

-continued
Method A

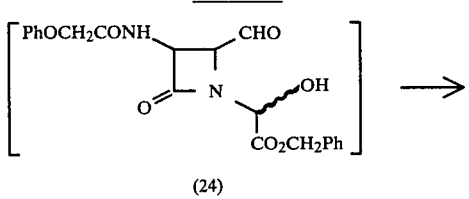

(24)

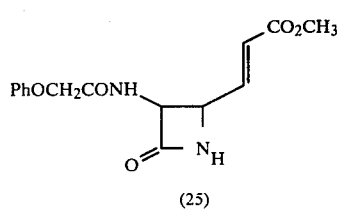

(25)

The β-lactam (23; 0.964 g) was kept at +5° for 16 h and 6 h at room temperature in a mixture of acetone (30 ml) and dilute hydrochloric acid (1.25 ml. 5 N). The solvent volume was reduced to a third and the solution was diluted with ethyl acetate, washed with sodium hydrogencarbonate solution, brine, dried (MgSO$_4$) and evaporated. The oily residue (24) was immediately taken up in methylene dichloride (25 ml) containing carbomethoxymethylenetriphenylphosphorane (1.05 g) and kept at room temperature for 21 h. The solvent was removed, and chromatography of the residue afforded the azetidinone (25; 0.32 g). m.p. 145°-147° (ethyl acetate) $\nu_{max.}$ (CHCl$_3$) 3425, 1785, 1730, 1695, 1650 sh cm$^{-1}$; δ ppm (CDCl$_3$) 3.68 (3H, s), 4.48 (2H, s, overlapping 1H, m), 5.43 (1H, m), 6.01 (1H, d, J 16 Hz), 6.8–7.8 (8H, m). (Found: C, 58.9; H, 5.3; N, 9.1; C$_{15}$H$_{16}$N$_2$O$_5$ requires C, 59.2; H, 5.3; N, 9.2%).

Method B

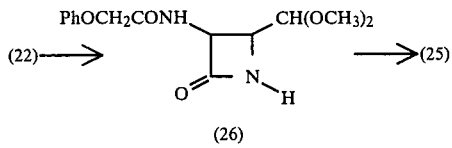

(26)

The acetal (22; 0.082 g) in dimethylformamide (0.8 ml), pyridine (0.8 ml) and water (0.32 ml) at 0° was oxidised with powdered potassium permanganate (0.040 g). After 1 h the mixture was diluted with ethyl acetate and a little water, and sulphur dioxide bubbled through to give a clear solution. The organic phase was carefully washed with dilute hydrochloric acid, dilute aqueous sodium hydrogencarbonate solution, brine dried (MgSO$_4$) and evaporated. Chromatography on silica H afforded the azetidinone (26; 0.010 g). $\nu_{max.}$ (CHCl$_3$) 3420, 1770, 1680 cm$^{-1}$. δ ppm (CDCl$_3$) 3.35 (3H, s), 3.41 (3H, s), 3.94 (1H, dd, J 3 and 6 Hz), 4.35 (1H, d, J 3 Hz), 4.51 (2H, s), 5.54 (1H, dd, J 6 and 10 Hz, each part shows some additional coupling J 1 Hz, lost on exch.), 5.81 b (1H, s, exch.) 6.7–7.6 (6H, m).

The azetidinone (26; 0.010 g) was kept in acetone (1 ml) containing dilute hydrochloric acid (5 N; 1 drop) for 1 h. The reaction was diluted with ethyl acetate, washed with dilute aqueous sodium hydrogencarbonate solution, dried (MgSO$_4$) and evaporated. The residue was dissolved in ethyl acetate (1 ml) containing carbomethoxymethylenetriphenylphosphorane (0.007 g) and left at ambient temperature for 16 h. Evaporation of the solvent and chromatography of the residue provided the azetidinone (25; 0.004 g), identical to that obtained by method A. An alternative procedure for the preparation of the azetidinone (25) is detailed in Examples (15) to (18).

EXAMPLE 15 cis 1-(1-Carbomethoxy-2-t-butyldimethylsilyloxyethyl)-4-styryl-3-triphenylmethylamino-azetidin-2-one (29)

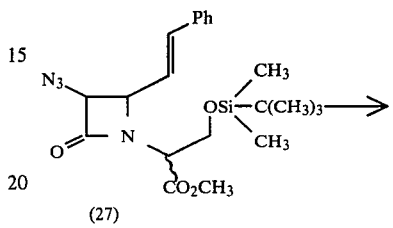

(27)

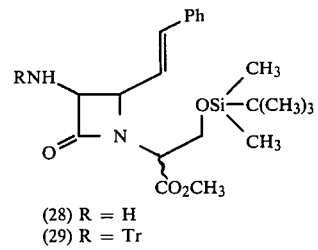

(28) R = H
(29) R = Tr

The β-lactam (27; 14.2 g), prepared from DL-serine using the procedure of G. Just and T-J. Liak [Canad. J. Chem. 56, 211 (1978)], was reduced to (28) as described in Example 3. Without further purification, the β-lactam (28) was stirred with triethylamine (5.02 ml) and triphenylmethyl chloride (10.1 g) in dry methylene dichloride at room temperature for 2.5 h. The reaction mixture was diluted with methylene dichloride, washed with water, dried (Na$_2$SO$_4$) and evaporated to a gum. Chromatography on silica H provided the required product (29; 15.62 g) as a yellow amorphous solid. $\nu_{max.}$ (CHCl$_3$) 1750, 1740, 1650 cm$^{-1}$; δ ppm (CDCl$_3$) −0.18 (3H, s), -0.12 (3H, s), 0.77, 0.82 (s, together 9H), 2.6 (1H, d, J 10 Hz, exch.), 3.57, 3.67 (s, together 3H), 3.8–4.8 (5H, m), 4.9–5.4 (1H, m), 6.0–6.3 (1H, m), 7.0–7.6 (20H, m). (Found: C, 73.8; H, 7.2; N, 4.5; C$_{40}$H$_{46}$N$_2$O$_4$Si requires C, 74.3; H, 7.1; N, 4.3%).

EXAMPLE 16 cis 1-(1-Methoxycarbonylvinyl)-4-styryl-3-triphenylmethylamino-azetidin-2-one (30)

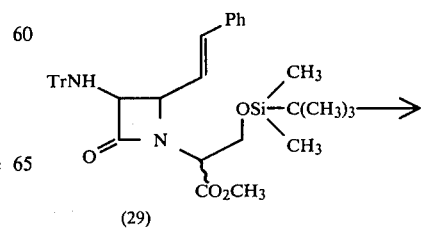

(29)

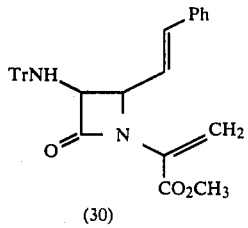

(30)

The β-lactam (29; 19 g) in dry tetrahydrofuran (280 ml) was vigorously stirred with tetraethylammonium fluoride (8.76 g) at room temperature under argon for 3.5 h. The mixture was poured into ethyl acetate and water, and the organic phase separated. The aqueous phase was extracted with ethyl acetate (×2), and the combined organic phases then washed with brine, dried (MgSO₄), and evaporated. Chromatography on silica H gave the product (30; 12.3 g) as an amorphous solid. $\nu_{max}$. (CHCl₃) 1750, 1730, 1720 cm⁻¹; δ ppm (CDCl₃) 2.61 (1H, d, J 11 Hz, exch.), 3.62 (3H, s), 4.48 (1H, dd, J 7 and 5 Hz), 4.60 (1H, dd, J 11 and 5 Hz), 5.02 (1H, dd, J 16 and 7 Hz), 5.80 (1H, s), 6.10 (1H, s), 6.11 (1H, d, J 16 Hz), 7.0–7.6 (20H, m). (Found: C, 78.8; H, 5.8; N, 5.4; C₃₄H₃₀N₂O₄ requires C, 79.4; H, 5.8; N, 5.5%).

EXAMPLE 17 cis 1-(1-Methoxycarbonylvinyl)-3-phenoxyacetamido-4-styryl-azetidin-2-one (32)

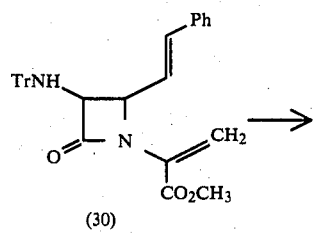

(30)

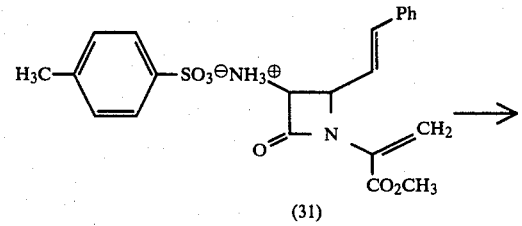

(31)

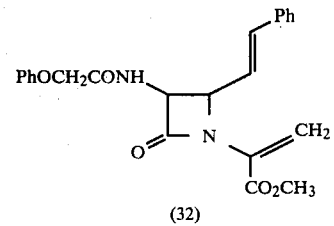

(32)

To the β-lactam (30; 3 g) in dry methylene dichloride (50 ml) was added b-toluenesulphonic acid dihydrate (1.23 g) in the minimum volume of methanol at −20°. After leaving the solution at +5° for 16 h, the solvent was removed and the crude p-toluene sulphonate (31) dried in vacuo.

The p.t.s.a. salt (31) was cooled to −20° in dry methylene dichloride (30 ml) and triethylamine (1.86 ml) added, followed by phenoxyacetyl chloride (0.89 ml) in methylene dichloride (5 ml) dropwise over 10 min. The reaction mixture was diluted with methylene dichloride, washed with brine, dried (MgSO₄), and evaporated. Chromatography of the residue on silica H provided that product (32; 1.96 g) as a white crystalline solid m.p. 151°–153° (ethyl acetate-light petroleum); $\nu_{max}$. (Nujol) 3285, 1755, 1730, 1675, 1610 cm⁻¹; δ ppm (CDCl₃) 3.76 (3H, s), 4.45 (2H, s), 5.24 (1H, dd, J 7 and 5 Hz), 5.50 (1 H, dd, J 5 and 8.8 Hz), 5.96 (1H, s), 6.04 (1H, dd, J 16.5 and 7 Hz), 6.16 (1H, s), 6.64 (1H, d, J 16.5 Hz), 6.9–7.4 (11H, m, reduced to 10H on exch.). (Found: C, 68.1; H, 5.4; N, 6.9; C₂₃H₂₂N₂O₅ requires C, 68.0; H, 5.4; N, 6.9%).

EXAMPLE 18 cis 4-(2-Methoxycarbonylvinyl)-3-phenoxyacetamido-azetidin-2-one (25)

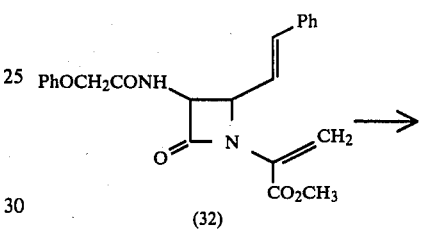

(32)

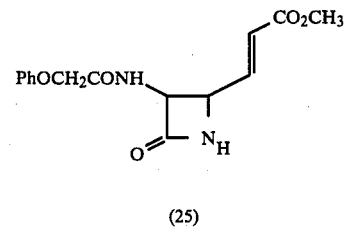

(25)

Ozonised oxygen was bubbled through a solution of the β-lactam (32; 1.47 g) in methylene dichloride (54 ml) and methanol (15 ml) at −76°. Excess ozone was removed by the passage of argon through the solution for 15 min, and tris-(p-methoxyphenyl)-phosphine (2.55 g) in a little methylene dichloride (10 ml) added. After 1 h carbomethoxymethylenetriphenylphosphorane (2.42 g) was added and the solution warmed to ambient temperature over 1 h. The solvent was removed and the residue chromatographed on silica H to give the desired product (25; 0.33 g) identical to that earlier described. An alternative intermediate (34) could be prepared as outlined in Example 19.

EXAMPLE 19 cis 3-Phenoxyacetamido-4-styryl-azetidin-2-one (34)

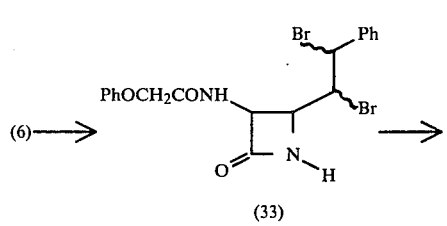

(33)

-continued

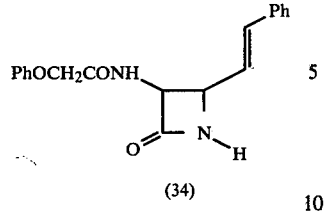

(34)

Powdered potassium permanganate (0.177 g) was added to the β-lactam (6; 0.5 g) in dimethylformamide (5 ml) and water (1 ml) at −20°. The reaction was warmed to 0° and after 1 h ethyl acetate was added, and sulphur dioxide passed through the mixture. The latter was washed with water, dilute hydrochloric acid, very dilute aqueous sodium hydrogencarbonate solution, brine, dried (MgSO₄) and evaporated to an amorphous solid (0.45 g). Chromatography on silica H yielded the azetidinone (33) as a white crystalline solid (0.13 g) m.p. 143°–145° (dec) (ethyl acetate-petroleum 60°–80°) $\nu_{max.}$ (Nujol) 3320, 1775, 1670 cm$^{-1}$; δ ppm (CDCl₃+(CD₃)₂SO) 4.07 (1H, dd, J 6.5 and 8.5 Hz), 4.60 (2H, s), 4.8–5.3 (4H, m), 6.5–7.5 (10H, m), 8.38 (1H, s), 8.80 (1H, d, J 8 Hz). (Found: C. 47.3; H, 3.4; N; 5.7; Br, 33.4; C₁₉H₁₈N₂O₃Br₂ requires C, 47.3; H, 3.7; N, 5.8; Br 33.2%).

Activated zinc dust (0.143 g) was added in one portion to the β-lactam (33; 0.09 g) in methylene dichloride (10 ml) and glacial acetic acid (1 ml) at room temperature. After 10 min the mixture was filtered, the filtrate diluted with methylene dichloride, washed successively with water, aqueous sodium hydrogencarbonate solution, brine, dried (MgSO₄) and evaporated to a white solid (0.06 g) (34) m.p. 181°–182° (ethyl acetate); $\lambda_{max.}$ (EtOH) 258 n.m. (ε 19,200); $\nu_{max.}$ (Nujol) 3290, 3225, 1780, 1730 and 1680 cm$^{-1}$; δ ppm ([CD₃]₂SO) (250 MHz) 4.43 (1H, dd, J 8.2 and 5 Hz), 4.49 and 4.57 (2H, ABq, J 15 Hz), 5.27 (1H, ddd, J 9.2, and ca. 0.5 Hz), 6.38 (1H, dd, J 16 and 8.2 Hz), 6.65 (1H, d, J 16 Hz), 6.8–7.5 (10H, m), 8.53 (1H, d, J ca. 0.5 Hz, exch. D₂O) and 8.88 (1H, d, J 9.2 Hz, exch. D₂O). (Found: C, 70.8; H, 5.7; N, 8.5. C₁₉H₁₈N₂O₃ requires C, 70.8; H, 5.6; N, 8.7%).

EXAMPLE 20 cis 1-(1-Hydroxy-1-p-nitrobenzyloxycarbonylmethyl)-4-(2-methoxycarbonylvinyl)-3-phenoxyacetamido-azetidin-2-one (35)

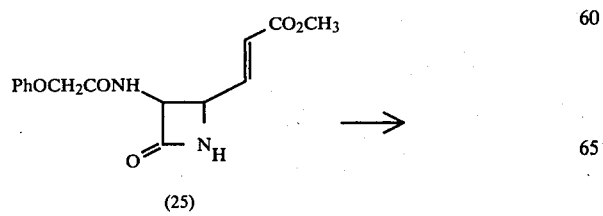

(25)

-continued

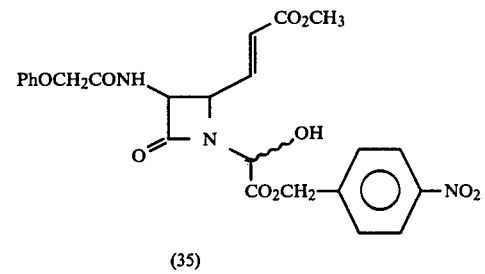

(35)

p-Nitrobenzylglyoxylate hydrate (0.49 g) was refluxed in dry benzene (12 ml) in a Dean-Stark apparatus to remove any water present, and then the azetidinone (25; 0.33 g) was added in dry dioxan (3–4 ml) and the mixture refluxed. After 12 h. the reaction mixture was cooled, and the solvent evaporated. The residual oil was chromatographed on silica H to give the glycolate (35; 0.44 g) as a white amorphous solid. $\lambda_{max.}$ (EtOH) 268 (δ 10700), 276 nm (9100); $\nu_{max.}$ (CHCl₃) 3430, 1775, 1720, 1700 cm$^{-1}$; δ ppm (CDCl₃) 3.68 (3H, s), 4.48 (2H, s), 4.5–4.75 (1H, m), 4.75–5.00 (1H, m, exch.), 5.20–5.50 (3H, m), 6.11 (1H, d, J 15 Hz), 6.5–7.75 (10H, m), 8.24 (1H, d, J 9 Hz). (Found: C, 55.8; H, 4.8; N, 7.8; C₂₄H₂₃N₃O₁₀ requires C, 56.1; H, 4.5; N, 8.2%).

EXAMPLE 21 cis 1-[2-Methoxycarbonyl-1-p-nitrobenzyloxycarbonyl-2-triphenylphosphoranylidene ethyl]-4-(2-methoxycarbonylvinyl)-3-phenoxyacetamido-azetidin-2-one (37)

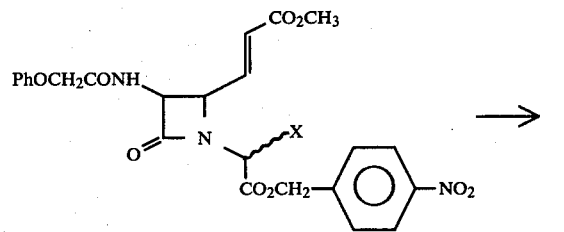

(35) X = OH
(36) X = Cl

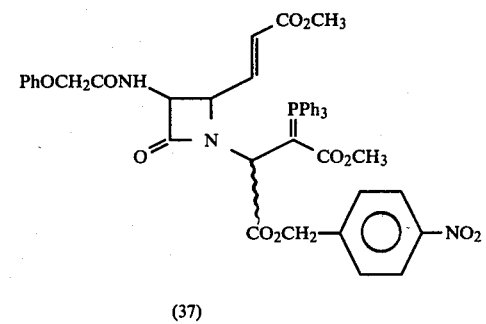

(37)

The hydroxy-ester (35; 0.43 g) was transformed into the phosphorane (37; 0.54 g) as described in Example 6. The product was an inseparable mixture of isomers. $\nu_{max.}$ (CHCl₃) 3430, 1755, 1740, 1720, 1690, 1620 cm$^{-1}$.

EXAMPLE 22

(2RS, 5RS, 6SR) p-Nitrobenzyl 1-aza-3-methoxycarbonyl-6-phenoxyacetamidobicyclo-[3.2.0]-hept-3-en-7-one-2-carboxylate (38)

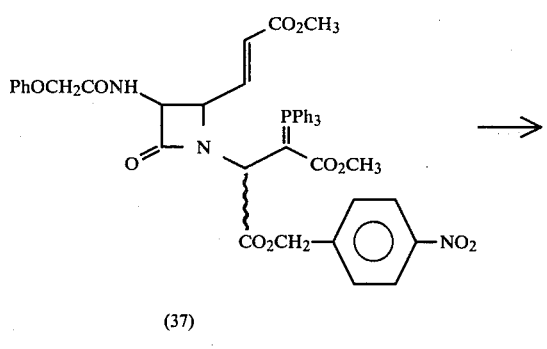

(37)

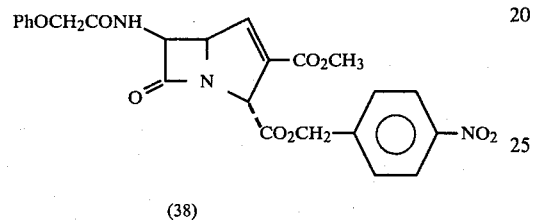

(38)

Trifluoracetic acid (0.6 ml) was added to the β-lactam (37; 0.3 g) in ethyl acetate (6 ml) and after 10 min the solution was ozonised at −76° as described in Example 7. The product (38; 0.089 g) was obtained as a white amorphous solid. $\lambda_{max}$. (EtOH) 264 nm ($\epsilon$ 12400); $\nu_{max}$. (CHCl$_3$) 3425, 1795, 1750, 1730, 1690 cm$^{-1}$; δ ppm (CDCl$_3$) 3.74 (3H, s), 4.54 (2H, s), 5.02 (1H, ddd, J 5.7, 3.5 and 1.5 Hz), 5.27 (2H, s), 5.43 (1H, dd, J 3.5 and 1.7 Hz), 5.56 (1H, dd, J 7 and 5.7 Hz) and 6.8–8.3 (11H, m). (Found: C, 58.0; H, 4.1; N, 8.3. C$_{24}$H$_{21}$N$_3$O$_9$ requires C, 58.2; H, 4.2; N, 8.5%).

EXAMPLE 23

(2RS, 5RS, 6SR) Sodium 1-aza-3-methoxycarbonyl-6-phenoxyacetamido-bicyclo-[3.2.0]-hept-3-en-7-one-2-carboxylate (39)

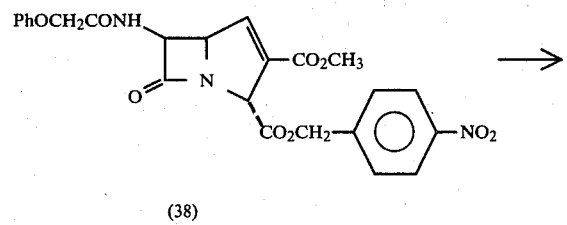

(38)

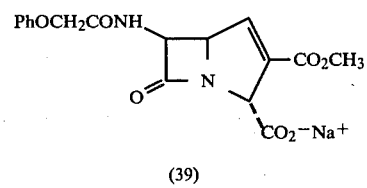

(39)

The ester (38; 0.04 g) was dissolved in dioxan (12 ml) and water (3 ml) and hydrogenated using 10% palladium/carbon catalyst (0.02 g). Sodium bicarbonate (0.0067 g) in water (0.15 ml) was added, the mixture filtered and the filtrate evaporated to remove the dioxan. The aqueous residue was washed with ethyl acetate and then evaporated to dryness. Re-evaporation from ethanol, followed by toluene gave a white solid (39; 0.028 g). $\lambda_{max}$. (EtOH) 268 ($\epsilon$ 2200), 275 nm (1700); $\nu_{max}$. (KBr) 3400 b, 1750, 1715, 1675, 1610 cm$^{-1}$. δ ppm (D$_2$O) 3.65 (3H, s), 4.79 (1H, m), 5.02 (1H, m), 5.33 (1H, m), 6.5–7.3 (7H, m). The side-chain methylene was obscured by the HOD peak.

EXAMPLE 24 cis 1-(1-Methoxycarbonylvinyl)-3-([N-p-nitrobenzyloxycarbonyl]-D-α-phenylglycylamino)-4-styryl-azetidin-2-one (40)

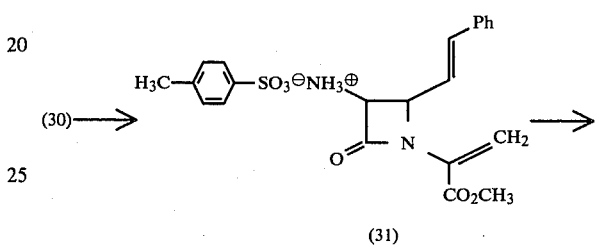

(31)

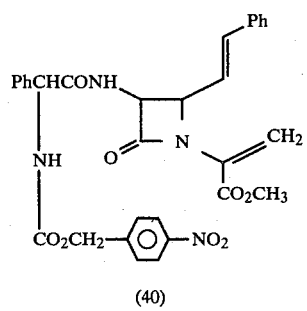

(40)

The lactam (30; 2 g) was detritylated as described in Example 17. To methyl chloroformate (0.445 g) in dry tetrahydrofuran (45 ml), cooled to −10°, was added, dropwise over 10 min, a solution of N-p-nitrobenzyloxycarbonyl-D-α-phenylglycine (1.42 g), triethylamine (0.44 g) and N,N-dimethyl benzylamine (2 drops), in dry tetrahydrofuran (20 ml). After 20 min triethylamine (0.597 ml) was added, with cooling, to the salt (31) in dry tetrahydrofuran (20 ml) and this solution then added dropwise over 10 min to the mixed anhydride at −10°. After a further 20 min the reaction mixture was filtered, the filtrate concentrated and the residue taken up in ethyl acetate, and washed successively with dilute hydrochloric acid, dilute sodium hydrogencarbonate solution, brine, dried (MgSO$_4$) and evaporated. Trituration of the residue with ether gave a white solid (40; 1.65 g) m.p. 176°–7° (ethyl acetate-light petroleum 60°–80°); max. (Nujol) 3280, 1760, 1725, 1690, 1655 cm$^{-1}$; δ ppm (CDCl$_3$) 3.73 (3H, s), 4.95–5.55 (3H, m), 5.09 (2H, s), 5.87 (1H, s), 6.02 (1H, s), 6.34 (1H, dd, J 16 and 8 Hz), 6.6–7.6 (14H, m), 8.12 (2H, d, J 8 Hz), 8.82 (1H, m). (Found: C, 63.7; H, 4.6; N, 9.4; C$_{31}$H$_{28}$N$_4$O$_8$ requires C, 63.7; H, 4.8; N, 9.6%).

EXAMPLE 25 cis 4-(2-Methoxycarbonylvinyl)-3-([N-p-nitrobenzyloxycarbonyl]-D-α-phenylglycylamino)-azetidin-2-one (41)

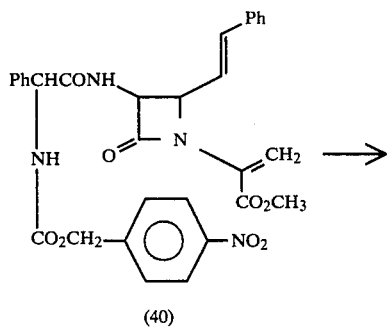

(40)

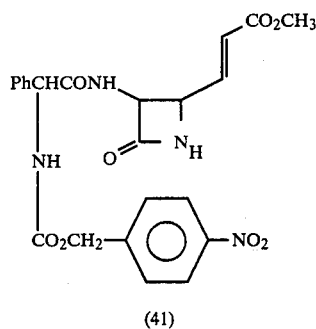

(41)

The lactam (40; 1.74 g) was treated as described in Example 18 to provide the azetidinone (41; 0.78 g). $\nu_{max}$. (CHCl$_3$) 3425, 3300b, 1770, 1720, 1690, 1610 cm$^{-1}$; δ ppm [(CD$_3$)$_2$CO+(CD$_3$)$_2$SO]0 3.67 (3H, s), 4.47 (1H, m), 5.22 (2H, s), 5.2–5.5 (2H, m, collapses to 1H, d, J8 Hz centered at 5.30 and 1H, s, 5.39, on exch.), 5.96 (1H, dd, J 10 and 15 Hz), 6.77 (1H, m), 7.2–7.8 (9H, m), 7.96 b, (1H, s, exch.), 8.20 (2H, d, J8 Hz), 8.63 (1H, m, exch.). (F.D. spectra gave an M$^+$+1 at 483, consistent with C$_{23}$H$_{22}$N$_4$O$_8$, requiring M 482).

EXAMPLE 26 cis 1-(1-Hydroxy-1-p-nitrobenzyloxycarbonylmethyl)-4-(2-methoxycarbonylvinyl)-3-([N-p-nitrobenzyloxycrbonyl]-D-α-phenylglycylamino)-azetidin-2-one (42)

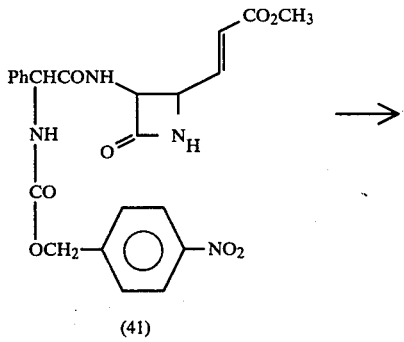

(41)

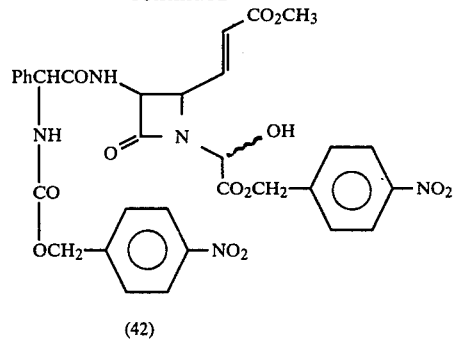

(42)

p-Nitrobenzylglyoxylate hydrate (1.47 g) was refluxed in dry benzene (50 ml) in a Dean-Stark apparatus to remove any water present, and then the azetidinone (41; 0.63 g) was added in dry dioxan (10 ml) and the mixture refluxed. After 23 h the reaction mixture was cooled and the solvent evaporated. The residual oil was chromatographed on silica H to give the glycolate (42; 0.54 g) as a white foam. $\nu_{max}$. (CHCl$_3$) 3425, 3325b, 1760, 1725, 1690, 1610 cm$^{-1}$.

EXAMPLE 27 cis 4-(2-Methoxycarbonylvinyl)-1-[2-methoxycarbonyl-1-p-nitrobenzyloxycarbonyl-2-triphenylphosphoranylidene ethyl]-3-[(N-p-nitrobenzyloxycarbonyl)-D-α-phenylglycylamino]azetidin-2-one (44)

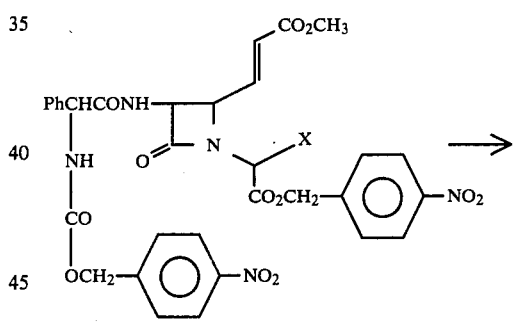

(42) X = OH
(43) X = Cl

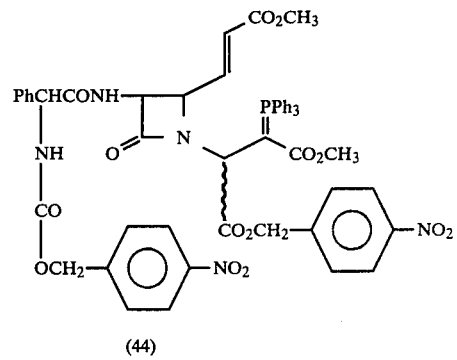

(44)

The hydroxy-ester (42; 0.77 g) was converted into the phosphorane (44; 0.64 g) as described in Example 6. The product was an inseparable mixture of isomers. $\nu_{max}$. (CHCl$_3$) 3425, 1760, 1725, 1690, 1620 cm$^{-1}$.

EXAMPLE 28

(2RS, 5RS, 6SR) p-Nitrobenzyl 1-Aza-3-methoxycarbonyl-6-[(N-p-nitrobenzyloxycarbonyl)-D-α-phenylglycylamino]-bicyclo [3.2.0]-hept-3-en-7-one-2-carboxylate (45) and cis 4-Formyl-1-[(1RS) 2-methoxycarbonyl-1-p-nitrobenzyloxycarbonyl-2-triphenylphosporanylidene ethyl]-3-[(N-p-nitrobenzyloxycarbonyl)-D-α-phenylglycylamino]-azetidin-2-one (46)

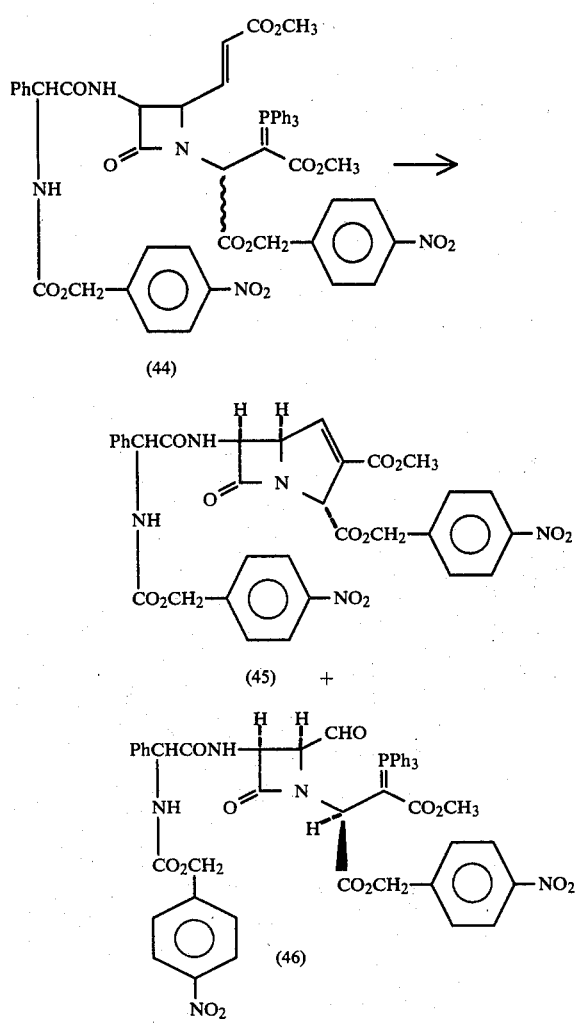

Trifluoroacetic acid (1.8 ml) was added to the β-lactam (44; 0.462 g) in ethyl acetate (18 ml) and after 10 min. the solution was ozonised as described in Example 7 to provide the product (45; 0.11 g) as a white amorphous solid. λ$_{max}$. (EtOH) 262 n.m. (ε 17,900); ν$_{max}$. (CHCl$_3$) 3420, 1795, 1730 b, 1690 sh, 1610 cm$^{-1}$; δ ppm (CDCl$_3$) 3.64 (3H, s), 4.87 (1H, ddd, J 6, 4, and 1.5 Hz), 5.13 (2H, s), 5.2–5.53 (3H, m), 5.23 (2H, s) 6.26 (1H, d, J 7 Hz, exch.), 6.38 (1H, d, J 1.5 Hz), 6.9 b (1H, s, exch.), 7.2–7.5 (9H, m), 8.08–8.25 (4H, m). (Found: C, 57.1; H, 4.3; N, 10.2; C$_{32}$H$_{27}$N$_5$O$_{12}$ requires C, 57.1; H, 4.0; N, 10.4%).

Further elution of the column provided the aldehyde (46; 0.19 g) contaminated with some triphenylphosphine oxide. ν$_{max}$. (CHCl$_3$) 3400 b, 1750, 1725, 1690, 1620, 1610 cm$^{-1}$.

EXAMPLE 29

(2SR, 5RS, 6SR) p-Nitrobenzyl 1-Aza-3-methoxycarbonyl-6-[(N-p-nitrobenzyloxycarbonyl)-D-α-phenylglycylamino]-bicyclo [3.2.0]-hept-3-en-7-one-2-carboxylate (47)

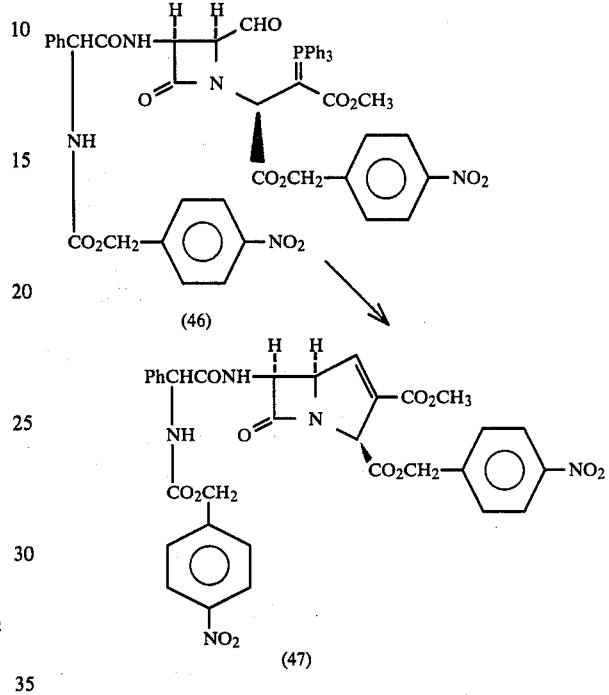

The aldehyde (46; 0.19 g contaminated with triphenylphosphine oxide) was gently refluxed in ethyl acetate for 10 h, the solution cooled and evaporated to give an oil. Chromatography on silica H provided the product (47; 0.06 g) as an amorphous white solid. λ$_{max}$. (EtOH) 263 nm (ε 20900); ν$_{max}$. (CHCl$_3$) 3425, 1790, 1725, 1690, 1610 cm$^{-1}$; δ ppm (CDCl$_3$) 3.64 (3H, s), 4.7–4.9 (2H, m), 5.16 (2H, s), 5.24 (2H, s), 5.35 (2H, m), 6.19 (1H, d, J 7 Hz, exch.), 6.34 (1H, s), 6.95 b (1H, m, exch.), 7.2–7.6 (9H, m), 8.08–8.30 (4H, m). (Found: C, 56.7; H, 3.9; N, 10.1; C$_{32}$H$_{27}$N$_5$O$_{12}$ requires C, 57.1; H, 4.0; N, 10.4%).

EXAMPLE 30

(2RS, 5RS, 6SR) 1-Aza-3-methoxycarbonyl-6-D-α-phenylglycylamino-bicyclo-[3.2.0]-hept-3-en-7-one-2-carboxylic acid, p-toluidine salt (48)

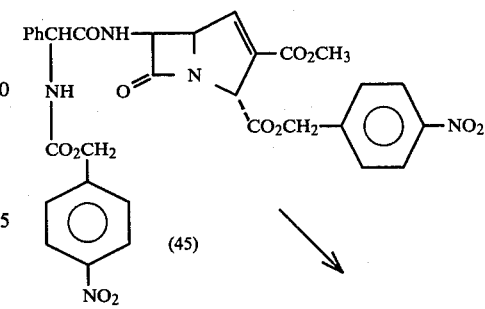

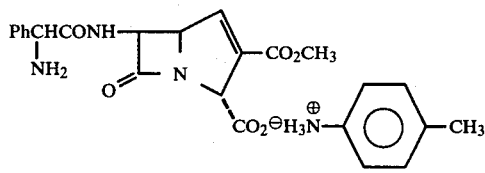

(48)

The ester (45; 25 mg) was dissolved in dioxan (12 ml) and water (3 ml) and hydrogenated using 10% Pd/C catalyst (12 mg). The reaction mixture was filtered, and the filtrate evaporated to dryness, followed by re-evaporation from ethanol, then toluene to give a solid. Trituration with ether provided the salt (48; 20 mg) as a pale yellow-green solid. $\lambda_{max}$. (EtOH) 250 ($\epsilon$ 5500), 256 nm (4900); $\nu_{max}$. (KBr) 3400b, 1750, 1720, 1690, 1610 cm$^{-1}$.

EXAMPLE 31 cis
3-DL-α-Benzyloxycarbonyl-phenylacetamido-1-(1-methoxycarbonylvinyl)-4-styrylazetidin-2-one (48)

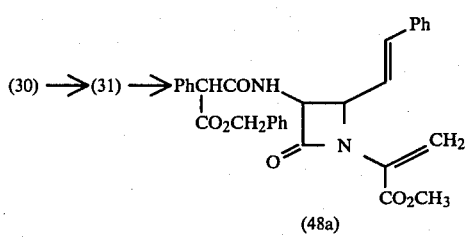

(48a)

Reaction of [31; prepared from (30; 4 g)] with freshly prepared DL-α-benzyloxycarbonyl phenylacetyl chloride (2.54 g) as described in Example 17 gave the acylamino derivative (48a; 3.7 g) as a white foam. $\nu_{max}$. (CHCl$_3$) 3350, 1760, 1730, 1682, 1615 cm$^{-1}$; δ ppm (CDCl$_3$) 3.71 (3H, s), 4.50 (0.5H, s), 4.52 (0.5H, s), 5.00 (1H, s), 5.07 (1H, s), 5.16 (1H, m), 5.41 (1H, m), 5.8–6.1 (1H, m, obscured by signal at δ 5.96), 5.96 (1H, d, J 2 Hz), 6.12 (1H, d, J 2 Hz), 6.53 (0.5H, d, J 16 Hz), 6.55 (0.5H, d, J 16 Hz), 6.9–7.4 (15H, m), 6.77 (1H, d, J 8 Hz, exch.) (Found: M+524.1937; C$_{31}$H$_{28}$N$_2$O$_6$ requires M 524.1944).

EXAMPLE 32 cis
3-DL-α-Benzyloxycarbonyl-phenylacetamido-4-(2-methoxycarbonylvinyl)-azetidin-2-one (49)

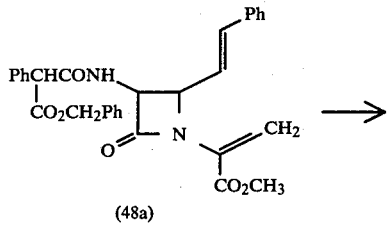 

(48a)

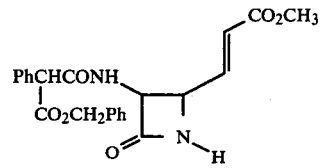

(49)

The β-lactam (48a; 1.57 g) was converted into the azetidinone (49; 0.54 g) as described in Example 18. $\nu_{max}$. (CHCl$_3$) 3420, 3325, 1778, 1728, 1685 cm$^{-1}$; δ ppm (CDCl$_3$) 3.64 (1.5H, s), 3.67 (1.5H, s), 4.41 (1H, m), 4.54 (0.5H, s), 4.58 (0.5H, s), 5.12 (2H, s), 5.30 (1H, m), 5.91 (0.5H, dd, J 15 and 1 Hz), 5.98 (0.5H, dd, J 15 and 1 Hz), 6.69 (0.5H, dd, J 15 and 6 Hz), 6.76 (0.5H, dd, J 15 and 6 Hz), 7.26 (5H, s), 7.4–7.9 b (2H, m, exch.). (Found: M+422.1471; C$_{23}$H$_{22}$N$_2$O$_6$ requires 422.1476).

EXAMPLE 33 cis
3-DL-α-Benzyloxycarbonyl-phenylacetamido-1-(1-hydroxy-1-p-nitrobenzyloxy carbonylmethyl)-4-(2-methoxycarbonylvinyl)-azetidin-2-one (50)

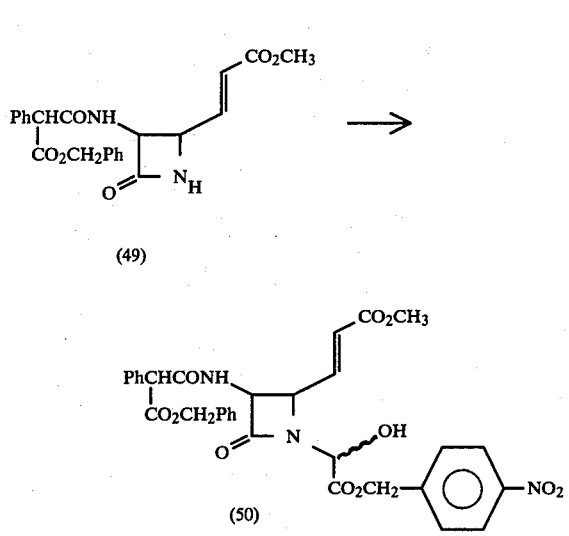

(50)

p-Nitrobenzylglyoxylate (0.523 g) was refluxed in dry benzene (25 ml) with provision for the azeotropic removal of water for 1 h, cooled and the azetidinone (49; 0.486 g) added in benzene (5 ml) and the mixture refluxed. After 9 h the reaction mixture was cooled, and the solvent evaporated. The residual oil was chromatographed on silica H to give the glycolate (50; 0.331 g) as a white foam. $\nu_{max}$. (CHCl$_3$) 3350b, 1775, 1755, 1725, 1680, 1610 cm$^{-1}$.

EXAMPLE 34 cis 3-DL-α-Benzyloxycarbonyl-phenylacetamido-4(2-methoxycarbonylvinyl)-1-[2-methoxycarbonyl-1-p-nitrobenzyloxycarbonyl-2-triphenylphosphoraneylidene-ethyl]-azetidin-2-one (52)

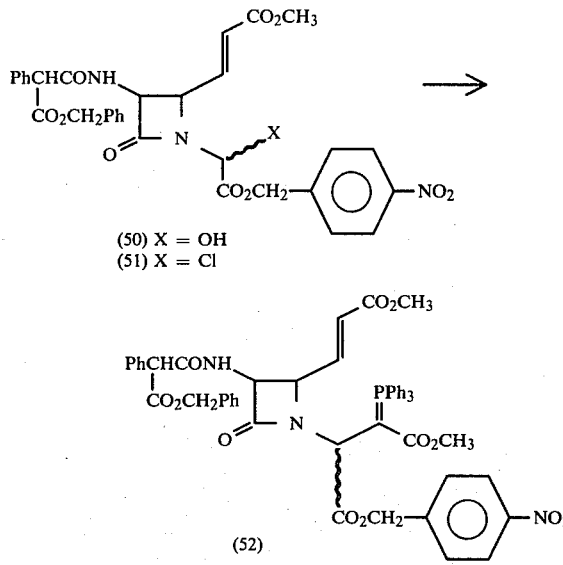

(50) X = OH
(51) X = Cl (52)

The glycolate (50; 0.268 g) was converted, via the chloride (51), into the phosphorane (52; 0.252 g) as described in Example 6. $\nu_{max}$ (CHCl$_3$) 3425, 1760, 1725, 1680, 1620 cm$^{-1}$.

EXAMPLE 35

(2RS, 5RS, 6SR) p-Nitrobenzyl] 1-Aza-6-(DL-α-benzyloxycarbonyl-phenylacetamido)-3-methoxycarbonyl-bicyclo-[3.2.0]-hept-3-en-7-one-2-carboxylate (53).

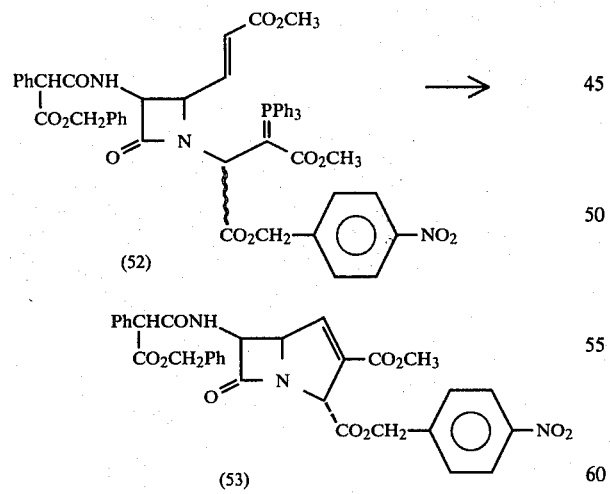

(52)

(53)

Trifluoroacetic acid (0.8 ml) was added to the β-lactam (52; 0.427 g) in ethyl acetate (8 ml) and after 10 min the solution ozonised as described in Example 7 to give the desired product (53; 0.061 g) as a white foam. $\lambda_{max}$ (EtOH) 260 nm (ε 11140); $\nu_{max}$ (CHCl$_3$) 3400, 1790, 1740, 1725, 1680, 1610 cm$^{-1}$; δ ppm (CDCl$_3$) 3.71 (3H, s), 4.53 (0.5H, s), 4.57 (0.5H, s), 4.93 (1H, m), 5.16 (2H, s), 5.24 (2H, s), 5.3–5.55 (2H, m), 6.66 (0.5H, m), 6.82 (0.5H, m), 6.8–7.2 (13H, m, reduces to 12 H on exch.), 8.20 (2H, m). (No molecular ion M+ was obtainable but the mass spectrum showed fragment ions at m/e 309 and 304 consistent with β-lactam cleavage of (53). Found: m/e 309.0992, C$_{18}$H$_{15}$NO$_4$ requires 309.1000; m/e 304.0714, C$_{14}$H$_{12}$N$_2$O$_6$ requires 304.0695).

EXAMPLE 36

(2RS, 5RS, 6SR) 1-Aza-6-(DL-α-benzyloxycarbonyl-phenylacetamido)-3-methoxycarbonylbicyclo [3.2.0]-hept-3-en-7-one-2-carboxylic acid, p-toluidine salt (54)

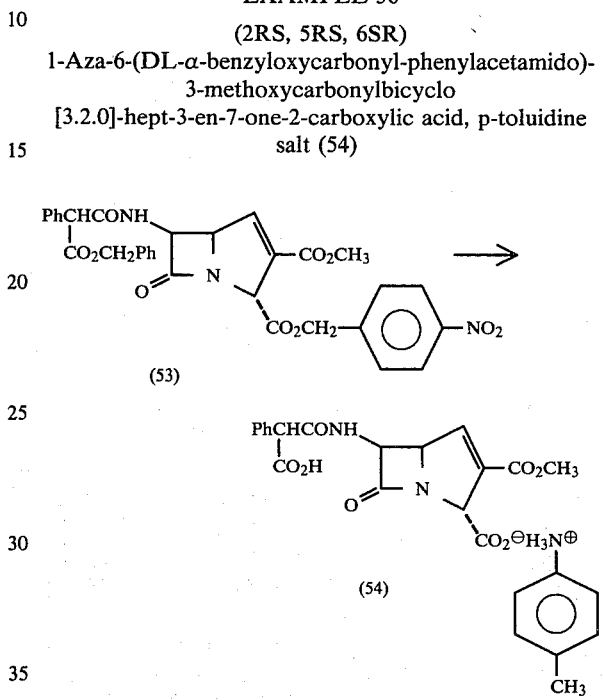

(53)

(54)

The ester (53; 50 mg) was hydrogenated as described in Example 30 to provide the salt (54; 40 mg) as an unstable gummy solid.

EXAMPLE 37 cis 1-[2-Cyano-1-p-nitrobenzyloxycarbonyl-2-triphenyl-phosphoranylidene ethyl]-4-(2-methoxycarbonylvinyl)-3-phenoxyacetamido-azetidine-2-one (55)

(35) → (36) →

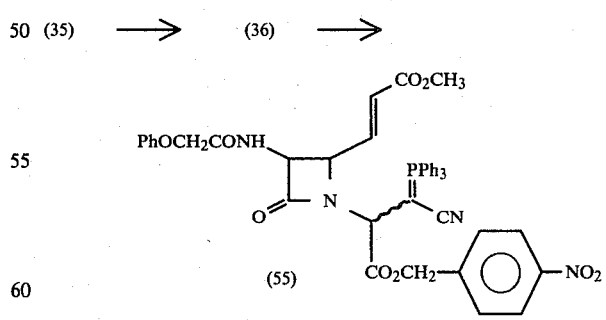

(55)

The glycolate (35; 2.5 g) was converted into (36) as described in Example 21. The total crude product (36) was dissolved in dry methylene dichloride (70 ml) containing cyanomethylenetriphenylphosphorane (2.93 g), and after 24 h the solvent was removed and the residue chromatographed on silica H to give the product (55;

EXAMPLE 38

(2RS, 5RS, 6SR) p-Nitrobenzyl 1-Aza-3-cyano-6-phenoxyacetamido-bicyclo-[3.2.0]-hept-3-en-7-one-2-carboxylate (56)

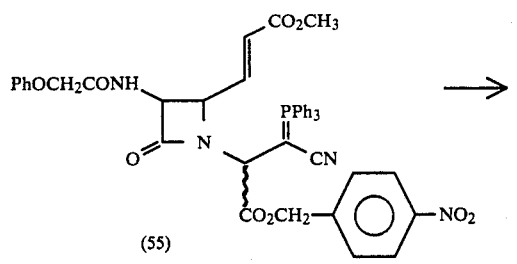

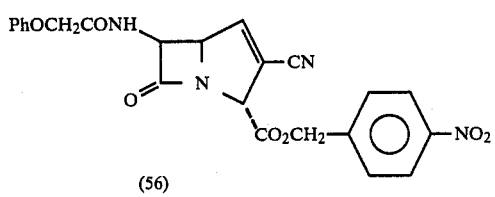

Trifluoroacetic acid (2.5 ml) was added to the β-lactam (55; 0.398 g) in ethyl acetate (25 ml) and after 7 min. the solution ozonised as described in Example 7 to provide the product (56; 0.048 g) as a white foam. $\nu_{max}$. (EtOH) 261 nm ($\epsilon$12100); $\nu_{max}$. (CHCl$_3$) 3400, 2220, 1798, 1755, 1690, 1610 cm$^{-1}$. δppm (CDCl$_3$) 4.52 (2H, s), 5.02 (1H, ddd, J 5.7, 3.6 and 2.0 Hz), 5.30 (2H, s), 5.37 (1H, dd, J 3.6 and 1.9 Hz), 5.54 (1H, dd, J 7.0 and 5.7 Hz), 6.65 (1H, dd, J 2.0 and 1.9 Hz), 6.98 (1H, d, J 7.0 Hz), 6.8–7.7 (7H, m), 8.25 (2H, m). (Found: M+ 462.1178; C$_{23}$H$_{18}$N$_4$O$_7$ requires M 462.1175).

EXAMPLE 39

(2RS, 5RS, 6SR) Sodium 1-aza-3-cyano-6-phenoxyacetamido-bicyclo[3.2.0]-hept-3-en-2-carboxylate (57)

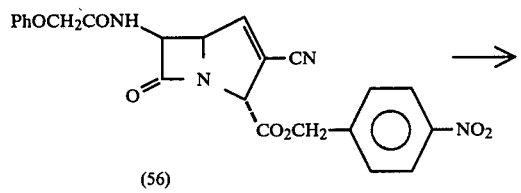

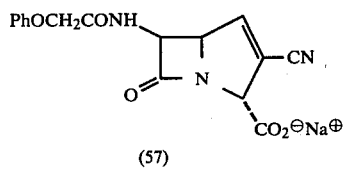

The ester (56; 0.05 g) was hydrogenated as described in Example 23, to give the sodium salt (57; 0.036 g) as an off-white solid. $\lambda_{max}$. (EtOH 268) ($\epsilon$2000) 275 nm (1700); $\nu_{max}$. (KBr) 3400 b, 2215 w, 1780, 1660, 1620 cm$^{-1}$.

| | Antibacterial Activity of 6-Acylamino-bicyclo-[3.2.0]-hept-3-en-7-ones | | | |
|---|---|---|---|---|
| | Minimum Inhibitory Concentration, μg/ml[a] | | | |
| Organism | (39) | (48) | (54) | (57) |
| E. coli | >100 | 50 | >100 | >50 |
| Klebsiella aerogenes | >100 | 50 | 100 | >50 |
| Proteus mirabilis | >100 | 25 | >100 | >50 |
| S. typhimurium | >100 | 12.5 | 100 | >50 |
| B. subtilis | 1.0 | 1.2 | 25 | 2.5 |
| Staph. aureus Oxford | 2.5 | 12.5 | >100 | 5.0 |
| Staph. aureus Russell[b] | >100 | >50 | >100 | 50 |
| Strep. faecalis | — | 12.5 | >100 | >50 |
| Strep. pneumoniae | — | 0.5 | 10 | 1.2 |

[a]Determined by serial dilution on DST agar containing 10% horse blood using an inoculum of 0.001 ml of a 10$^{-2}$ dilution for Gram-positive bacteria or a 10$^{-4}$ dilution for Gram-negative organisms. MIC values were read after incubation at 37° C. for 18 h.

[b]β-Lactamase-producing benzylpenicillin-resistant strain.

EXAMPLE 40

N-Cinnamylidene-p-methoxymethoxyaniline (59)

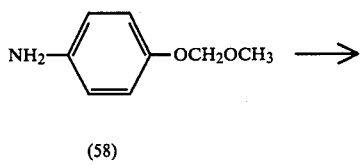

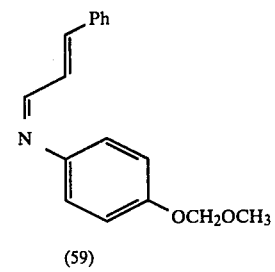

p-Methoxymethoxyaniline (58: T. Fukuyama, R. K. Frank and C. F. Jewell, Jr., J. Amer. Chem. Soc., 1980, 102, 2122) (13.8 g) was dissolved in dry methylene chloride (200 ml) under argon, and cinnamaldehyde (13.3 g) and dry magnesium sulphate (10 g) added. The mixture was stirred at room temperature for 15 h, filtered, and the filtrate evaporated to give a yellow solid (59) (24 g) m.p. 88°–88.5° (ethyl acetate/light petroleum) $\lambda_{max}$. (EtOH) 296 ($\epsilon$23,245) and 345 n.m. (23, 206); $\nu_{max}$. (CHCl$_3$) 1625 and 1605 cm$^{-1}$; νp.p.m. (CDCl$_3$) 3.47 (3H, s), 5.16 (2H, s), 6.95–7.6 (9H, m), 8.28 (1H, dd, J 2 and 4 Hz). (Found: C, 76.1; H, 6.5; N, 5.0; C$_{17}$H$_{17}$NO$_2$ requires C, 76.4; H, 6.4; N, 5.2%).

EXAMPLE 41 cis 3-Azido-1-(p-methoxymethoxyphenyl)-4-styryl-azetidin-2-one (60)

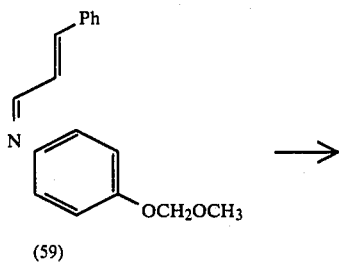

(59)

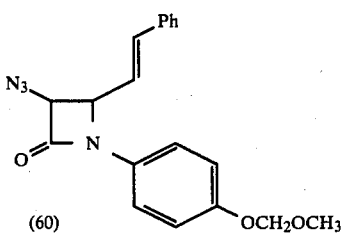

(60)

The Schiff base (59) (24 g) was converted into (60) (26.1 g) as described in Example 2, m.p. 111°–112° C.; (ethyl acetate/light petroleum) $v_{max}$. (CHCl$_3$) 2120, 1755 and 1650 cm$^{-1}$; δppm (CDCl$_3$) 3.38 (3H, s), 4.7–4.95 (2H, m), 5.06 (2H, s), 6.19 (1H, dd, J 7 and 17 Hz), 6.81 (1H, d, J 17 Hz) and 6.9–7.5 (9H, m). (Found: C, 65.1; H, 5.1; N, 15.9; C$_{19}$H$_{18}$N$_4$O$_3$ requires C, 65.1; H, 5.1; N, 16.0%).

EXAMPLE 42 cis 3-Azido-4-styryl-azetidin-2-one (61)

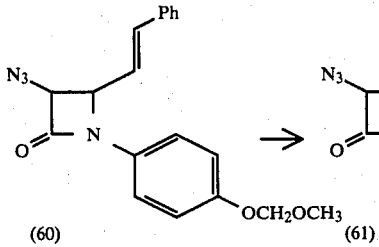

The lactam (60) (350 mg) in tetrahydrofuran (10 ml) was cooled to 0° C. and ceric ammonium nitrate (274 g) in water (4 ml) added dropwise over 2–3 min to the vigorously stirred solution (see ref. in Example 40). After 10 min. solid sodium sulphite was added to decolourise the mixture, which was then poured into ethyl acetate and dilute sodium hydrogencarbonate. The organic layer was separated, washed with brine, dried and evaporated. Chromatography of the residue on silica afforded the product (61) (149 mg), m.p. 106° (ethyl acetate/light petroleum) $v_{max}$. (CHCl$_3$) 3400, 2110, 1775 and 1650 cm$^{-1}$; δppm (CDCl$_3$) 4.48 (1H, dd, J 4.4 and 7 Hz), 4.81 (1H, dd, J 1.8 and 4.4 Hz, becomes d, J 4.4 Hz on irradiation at δ6.56), 6.19 (1H, dd, J 7 and 16 Hz), 6.56 b (1H, s), 6.69 (1H, d, J 16 Hz) and 7.2–7.5 (5H, m). (Found: C, 61.7; H, 4.7; N, 25.9; C$_{11}$H$_{10}$N$_4$O requires C, 61.7; H, 4.7; N, 26.2%).

EXAMPLE 43 cis 3-Phenoxyacetamido-4-styryl-azetidin-2-one (34)

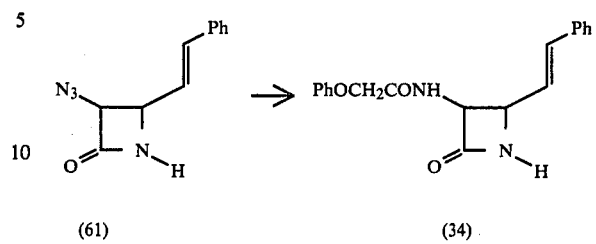

The azide (61) (75 mg) was dissolved in dry methylene chloride (10 ml) at 0° C., and triethylamine (80 mg) added. Hydrogen sulphide was bubbled through the solution for 5 min. and the solution allowed to warm to room temperature. After 2 h the solvent was evaporated, the residue dissolved in methylene chloride and the process repeated.

The crude amine was dissolved in methylene chloride at −10° C. and triethylamine (44 mg) added, followed by phenoxyacetyl chloride (65 mg) in methylene chloride (1 ml). The solution was washed with dilute citric acid, brine, dried and evaporated. Chromatography on silica eluting with methylene chloride/ethyl acetate gave the product (34) (70 mg), identical in all respects to that obtained in Example 19.

EXAMPLE 44 cis 3-Azido-1-(1-hydroxy-1-p-nitrobenzyloxycarbonylmethyl)-4-styryl-azetidin-2-one (62)

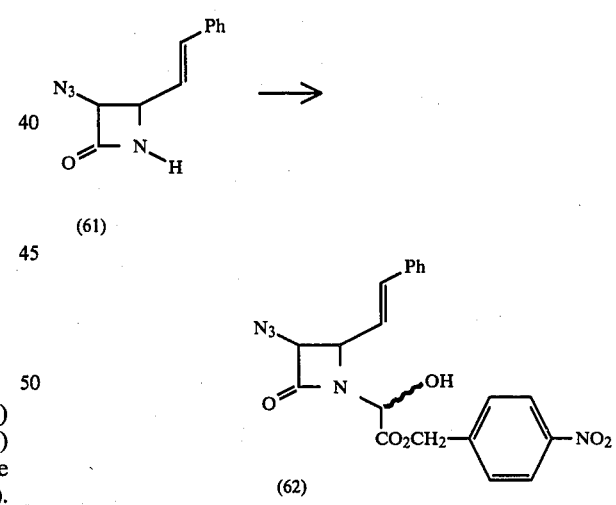

The azetidinone (61) (586 mg) and p-nitrobenzylglyoxylate monohydrate (1.2 g) were refluxed in benzene (100 ml) for 17 h, with provision for the removal of water. The cooled solution was evaporated and chromatographed to provide the less polar isomer (62) (325 mg) m.p. 134°–136°, $v_{max}$. (Nujol) 3420, 3380, 2095, 1750, 1740, 1650, 1520 and 1350 cm$^{-1}$; δppm (CDCl$_3$+[CD$_3$]$_2$SO) 4.68 (1H, dd, J 8 and 5 Hz), 4.87 (1H, d, J 5 Hz), 5.33 (2H, s), latter signal obscures a broad singlet which becomes 1H, s, at 5.28 on D$_2$O exch., 6.20 (1H, dd, J 16 Hz and 8 Hz), 6.75 b (1H, s, exch. D$_2$O), 6.72 (1H, d, J 16 Hz), 7.32 (5H, s), 7.55 (2H, d, J 8.5 Hz) and 8.18 (2H, d, J 8.5 Hz. (Found: C, 56.7;

H, 4.1; N, 16.2. $C_{20}H_{17}N_5O_6$ requires C, 56.7; H, 4.0; N, 16.5%).

Further elution provided the more polar isomer (62) (387 mg) m.p. 142° C.; $\nu_{max.}$ (Nujol) (CHCl$_3$) 3420, 3380, 2120, 1760 1750, 1650, 1520 and 1350 cm$^{-1}$; δppm (CDCl$_3$+2 drops [CD$_3$[$_2$SO) 4.72 (1H, dd, J 9 and 5 Hz), 4.89 (1H, d, J 5 Hz), 5.08 (2H, AA′ system), 5.68 (1H, d, J 6 Hz becomes s on D$_2$O exch.), 5.98 (1H, dd, J 16 and 9 Hz), 6.53 (1H, d, J 6 Hz, exch D$_2$O), 6.7 (1H, d, J 16 Hz), 7.25 (s, 5H), 7.35 (1H, d, 8.5 Hz) and 8.08 (1H, d, J 8.5 Hz. (Found: C, 56.4; H, 4.0; N, 16.2%).

Mixed fractions (62) (387 mg) were also obtained.

EXAMPLE 45

(1′RS,3SR,4RS) and (1′RS,3RS,4SR)-3-Azido-1-(2′-methoxycarbonyl-1′-p-nitrobenzyloxycarbonyl-2′-triphenylphosphoranylidene-ethyl)4-styryl-azetidin-2-one (64) and (65)

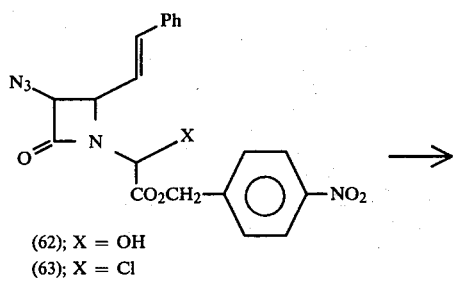

(62); X = OH
(63); X = Cl

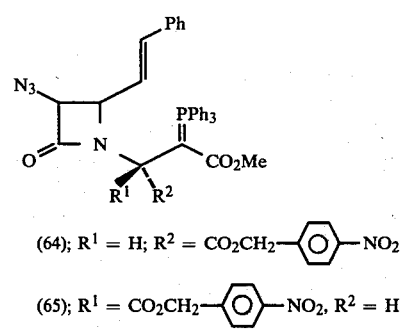

(64); R$^1$ = H; R$^2$ = CO$_2$CH$_2$—⟨⟩—NO$_2$ (65); R$^1$ = CO$_2$CH$_2$—⟨⟩—NO$_2$, R$^2$ = H

The hydroxy-ester (62) (395 mg) (either isomer) was converted into the phosphoranes (64) (128 mg) $\nu_{max.}$ (CHCl$_3$), 2105, 1760, 1740 sh, 1620, 1520 and 1350 cm$^{-1}$ and (65) (127 mg) $\nu_{max.}$ (CHCl$_3$) 2110, 1755 br, 1615, 1525 and 1350 cm$^{-1}$ as described in Example 6.

EXAMPLE 46

(2RS,5RS,6SR) p-Nitrobenzyl 1-Aza-6-azido-3-methoxycarbonyl-bicyclo[3.2.0]-hept-3-ene-7-one-2-carboxylate (66)

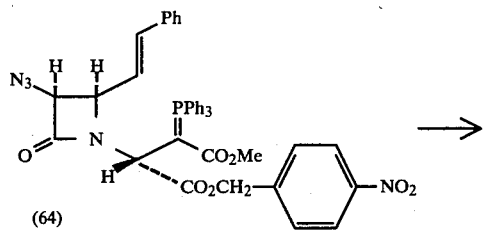

(64)

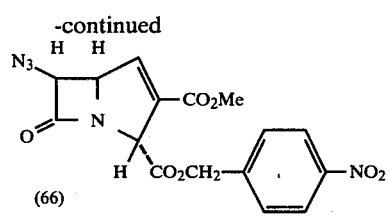

(66)

Trifluoroacetic acid (0.8 ml) was added to the β-lactam (64) (120 mg) in dry methylene chloride (9 ml) and after 10 min. the solution was ozonised as described in Example 7. After purging with argon dimethyl sulphide (0.3 ml) was added and the solution allowed to warm to 0° C. and carefully neutralised with sodium hydrogencarbonate. The organic phase was separated, washed with brine and dried (MgSO$_4$). After 2 h at room temperature the drying agent was removed and the solution evaporated and chromatographed to give the required product (66) as a gummy solid (43 mg), $\nu_{max.}$ (CHCl$_3$), 2110, 1795, 1750, 1730, 1520 and 1350 cm$^{-1}$; δppm (CDCl$_3$) (250 M Hz), 4.91 (1H, ddd, J 5.5, 3.5 and 1.5 Hz), 5.14 (1H, d, J 5.5 Hz), 5.26 and 5.32 (2H, ABq, J 13.2 Hz), 5.46 (1H, dd, J 3.5 and 1.8 Hz), 7.06 (1H, dd, J 1.8 and 1.5 Hz), 7.53 (2H, J 8.2 Hz) and 8.24 (2H, d, J 8.2 Hz).

Compound (66) may be converted to the amino compound (67):

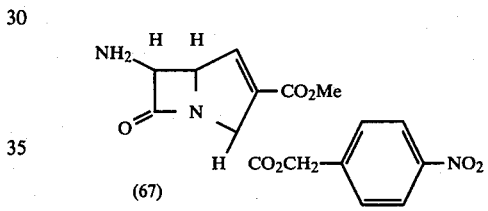

(67)

using Aluminium amalgam.

What we claim is:

1. A compound of the formula (II):

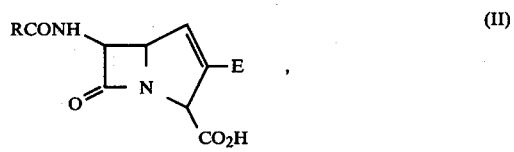 (II)

a pharmaceutically acceptable salt thereof or an ester thereof cleavable by hydrogenolysis or hydrolyzable in-vivo wherein RCONH is a group of the subformula (a), (b), (c) or (d):

$$A_5—(CH_2)_n—\underset{\underset{X}{|}}{CH}—(CH_2)_m—CO—NH \qquad (a)$$

$$A_6—CO—NH \qquad (b)$$

 (c)

$$A_6—X_2—(CH_2)_n—CO—NH \qquad (d)$$

wherein n is 0, 1 or 2; m is 0, 1 or 2; A$_5$ is alkyl of 1 to 6 carbon atoms, cycloalkyl of 3 to 6 carbon atoms, cyclohexenyl, cyclohexadienyl, phenyl, hydroxyphenyl, thienyl or pyridyl; X is hydrogen, bromo, chloro, a carboxylic acid moiety, a carboxylate ester cleavable by hydrogenolysis or hydrolyzable in-vivo, hydroxy, acyloxy, amino, ureido, guanidino or acylureido; $A_6$ is phenyl, 2,5-dimethoxyphenyl, 2-alkoxy-1-naphthyl, 3-arylisoxazolyl, isothiazolyl or 3-aryl-5-methylisoxazolyl wherein aryl is phenyl; $X_1$ is $CH_2OCH_2$, $CH_2SCH_2$ or $(CH_2)_n$ wherein n is as above defined; and $X_2$ is an oxygen or sulphur atom, and E is a carboxy group, a pharmaceutically acceptable salt thereof, an alkyl ester thereof wherein the alkyl moiety is of 1 to 10 carbon atoms and is unsubstituted or substituted by alkoxy of 1 to 7 carbon atoms, alkanoyloxy of 1 to 7 carbon atoms, alkenyl of up to 5 carbon atoms or alkynyl of up to 5 carbon atoms, or by 1 or 2 phenyl moieties each of which is unsubstituted or substituted by fluoro, chloro, bromo, nitro, alkyl of up to 4 carbon atoms or alkoxy of up to 4 carbon atoms, or E is cyano.

2. A compound according to claim 1 wherein E is alkoxycarbonyl of 1 to 10 carbon atoms unsubstituted or substituted by alkoxy of 1 to 7 carbon atoms, alkanoyloxy of 1 to 7 carbon atoms, alkenyl of up to 5 carbon atoms or alkynyl of up to 5 carbon atoms, or by 1 to 2 phenyl moieties each of which is unsubstituted or substituted by fluoro, chloro, bromo, nitro, alkyl of up to 4 carbon atoms or alkoxy of up to 4 carbon atoms or E is cyano.

3. A compound according to claim 2 wherein E is a group of the sub-formula (L) or (M):

$CO_2B_1$ <span>(L)</span>

$CO_2CHB_2B_3$ <span>(M)</span> wherein $B_1$ is alkyl of 1 to 6 carbon atoms unsubstituted or substituted by alkoxy of 1 to 7 carbon atoms or alkanoyloxy of 1 to 7 carbon atoms, $B_2$ is alkenyl of up to 5 carbon atoms, alkynyl of up to 5 carbon atoms or phenyl unsubstituted or substituted by fluoro, chloro, bromo, nitro or alkyl or alkoxy of up to 4 carbon atoms; and $B_3$ is hydrogen, alkyl of up to 4 carbon atoms or phenyl unsubstituted or substituted by fluoro, chloro, bromo, nitro or alkyl or alkoxy of up to 4 carbon atoms.

4. A compound according to claim 3 wherein E is methoxycarbonyl.

5. A compound according to claim 2 wherein E is cyano.

6. A compound according to claim 1 wherein RCONH is a group of the sub-formula (e) or (f):

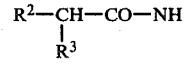  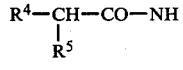

(e)            (f)

wherein $R^2$ is phenyl, thienyl or phenoxy; $R^3$ is hydrogen or methyl; $R^4$ is phenyl, p-hydroxyphenyl, thienyl or cyclohexadienyl; and $R^5$ is hydroxy, amino, a carboxylic acid moiety, phenyl, methylphenyl, indanyl or an alkyl ester thereof of 1 to 6 carbon atoms.

7. A compound according to claim 6 wherein RCONH is phenoxyacetamido, phenylacetamido, α-aminophenylacetamido or α-carboxyphenylacetamido.

8. A compound according to claim 3 wherein $B_1$ is alkyl of 1 to 6 carbon atoms.

9. A compound according to claim 3 wherein $B_1$ is methyl, ethyl, propyl, isopropyl, butyl, isobutyl, sec-butyl, tert-butyl, pentyl, neopentyl, isopentyl or hexyl.

10. A compound according to claim 3 wherein $B_1$ is methyl, ethyl or propyl.

11. A compound according to claim 3 wherein $B_1$ is methyl.

12. A compound according to claim 3 wherein $B_3$ is hydrogen and $B_2$ is phenyl unsubstituted or substituted by fluoro, chloro, bromo, nitro, alkyl of up to 4 carbon atoms or alkoxy of up to 4 carbon atoms.

13. A compound according to claim 3 wherein $CHB_2B_3$ is benzyl, methoxybenzyl, ethoxybenzyl, nitrobenzyl or chlorobenzyl.

14. A compound according to claim 1 wherein RCONH is phenylacetamido, p-hydroxyphenylacetamido, o-hydroxyphenylacetamido, m-hydroxyphenylacetamido, α-chlorophenylacetamido, α-bromophenylacetamido, α-carboxyphenylacetamido or the methylphenyl, indanyl or phenyl ester thereof, α-azidophenylacetamido, α-aminophenylacetamido, α-hydroxyphenylacetamido, α-ureidophenylacetamido, α-guanidinophenylacetamido, α-(acetyluredio)phenylacetamido, α-acetoxyphenylacetamido, α-tetrazolylphenylacetamido, acetamido, chloroacetamido, bromoacetamido, propionamido, pyridylacetamido, 2-thienylacetamido, 3-thienylacetamido, 2-thienylpropionamido, 3-thienylpropionamido, α-chloro(p-hydroxyphenyl)acetamido, α-bromo(p-hydroxyphenyl)acetamido, α-carboxy(p-hydroxyphenyl)acetamido or the methyl, phenyl, indanyl or phenyl ester thereof, α-amino(p-hydroxyphenyl)acetamido, α-hydroxy(p-hydroxyphenyl)acetamido, α-acetoxy(p-hydroxyphenyl)acetamido, α-ureido(p-hydroxyphenyl)acetamido, α-guanidino(p-hydroxyphenyl)acetamido, α-acetylureido(p-hydroxyphenyl)acetamido, phenoxyacetamido, o-hydroxyphenoxyacetamido, m-hydroxyphenoxyacetamido, p-hydroxyphenoxyacetamido, methoxyacetamido, ethoxyacetamido, α-amino(p-hydroxy)phenoxyacetamido, α-aminophenoxyacetamido, α-acetylphenoxyacetamido, α-acetyl(p-hydroxy)phenylacetamido, α-hydroxyphenoxyacetamido, α-hydroxy(p-hydroxy)-phenylacetamido, α-carboxyphenoxyacetamido or the methylphenyl, indanyl or phenyl ester thereof, α-carboxyl(p-hydroxy)phenoxyacetamido or the methylphenyl, indanyl or phenyl ester thereof, phenoxypropionamido, phenoxybutyramido, benzamido, 2,6-dimethoxybenzamido, 2-ethoxy-1-naphthamido, 2-methoxy-1-naphthamido, 2-propoxy-1-naphthamido, 3-phenyl-5-methyl-4-isoxazolylcarboxamido, 3-o-chlorophenyl-5-methyl-4-isoxazolylcarboxamido, 3-o,o-dichlorophenyl-5-methyl-4-isoxazolylcarboxamido, isothiazolylcarboxamido, 3-o,o-fluorochlorophenyl-5-methyl-4-isoxazolylcarboxamido, 3-phenyl-4-isoxazolylcarboxamido, 3-o-chlorophenyl-4-isoxazolyl-carboxamido, 3-o,o-dichlorophenyl-4-isoxazolylcarboxamido, 3-o,o-fluorochlorophenyl-4-isoxazolylcarboxamido, 1-aminolcyclohexyl-1-carboxamido, phenylthioacetamido, phenylthiopropionamido or p-hydroxyphenylthioacetamido.

15. A compound according to claim 14 wherein RCONH is phenylacetamido.

16. A compound according to claim 1 wherein RCONH is α-methylphenoxyacetamido, α-methylphenylacetamido, α-methyl-2-thienylacetamido, α-methyl-3-thienylacetamido, 2-thienylacetamido, 3-thienylacetamido, α-hydroxyphenylacetamido, α-hydroxy(p-hydroxyphenyl)acetamido, α-hydroxy-2- thienylacetamido, α-hydroxy-3-thienylacetamido, α-aminophenylacetamido, α-amino(p-hydroxyphenyl)acetamido, α-amino-3-thienylacetamido, α-amino-2-thienylacetamido, α-carboxyphenylacetamido, α-carboxy(p-hydroxyphenyl)acetamido, α-carboxy-2-thienylacetamido, α-carboxy-3-thienylacetamido or the methyl, ethyl propyl, butyl, phenyl, methylphenyl or indanyl ester of α-carboxyphenylacetamido, the methyl, ethyl, propyl, butyl, phenyl, methylphenyl or indanyl ester of α-carboxy (p-hydroxyphenylacetamido), the methyl, ethyl, propyl, butyl, phenyl, methylphenyl or indanyl ester of α-carboxy-2-thienylacetamido or the methyl, ethyl, propyl, butyl, phenyl, methylphenyl or indanyl ester of α-carboxy-3-thienylacetamido.

17. A compound according to claim 1 of the formula (III):

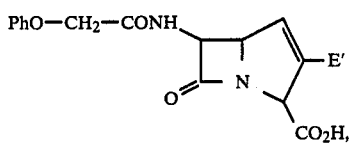

a pharmaceutically acceptable salt thereof or a cleavable ester thereof, wherein E' is methoxycarbonyl or cyano.

18. A compound according to claim 1 of the formula (IV):

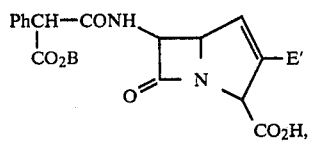

a pharmaceutically acceptable salt thereof or cleavable ester thereof, wherein E' is methoxycarbonyl or cyano and B is a cation, hydrogen, benzyl, phenyl, methylphenyl or indanyl.

19. A compound according to claim 1 of the formula (V):

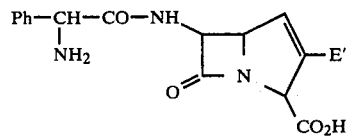

a pharmaceutically acceptable salt thereof or a cleavable ester thereof, wherein E' is methoxycarbonyl or cyano.

20. A compound according to claim 1 in the form of a pharmaceutically acceptable salt wherein said salt is an aluminum, sodium, potassium, calcium, magnesium, ammonium or substituted ammonium salt.

21. A salt according to claim 20 wherein the salt is the p-toluidine salt.

22. A salt according to claim 20 wherein the salt is the sodium, potassium, calcium or magnesium salt.

23. A salt according to claim 20 wherein the salt is the sodium salt.

24. A salt according to claim 20 wherein the salt is the potassium salt.

25. A compound according to claim 1 in the form of the free acid.

26. A compound according to claim 1 in zwitterionic form.

27. A compound according to claim 1 in the form of a di-acid.

28. A compound according to claim 1 in the form of a di-pharmaceutically acceptable salt.

29. A compound according to claim 1 in the form of an ester wherein the ester is a benzyl ester wherein the phenyl moiety is unsubstituted or substituted by alkyl of 1 to 6 carbon atoms, alkoxy of 1 to 6 carbon atoms, chloro, bromo or nitro.

30. A compound according to claim 1 in the form of an ester wherein the ester is the p-nitrobenzyl ester.

31. A compound according to claim 1 in the form of an ester wherein the ester is of the sub-formulae (g), (h) or (j):

 (g)

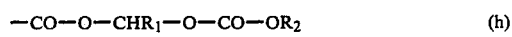 (h)

 (j)
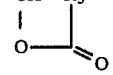

wherein $R_1$ is hydrogen or methyl; $R_2$ is alkyl of up to 4 carbon atoms, phenyl or benzyl; and $R_3$ is —CH=CH—, 1,2-phenylene or 4,5-dimethoxy-1,2-phenylene.

32. A compound according to claim 1 in the form of an ester wherein the ester is the acetoxylmethyl, pivaloyloxymethyl, α-acetoxyethyl, α-pivaloyloxyethyl, α-ethoxycarbonyloxyethyl, phthalidyl or 3,4-dimethoxyphthalidyl.

33. An ester according to claim 32 wherein the ester is phthalidyl.

34. A pharmaceutical composition useful for treating bacterial infections in animals including humans which comprises an antibacterially effective amount of a compound of the formula (II):

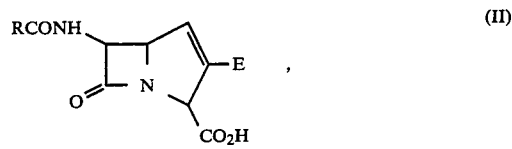

a pharmaceutically acceptable salt thereof or an ester thereof cleavable by hydrogenolysis or hydrolyzable in-vivo wherein RCONH is a group of the sub-formula (a), (b), (c) or (d):

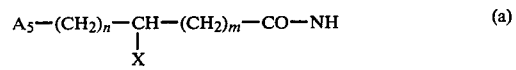 (a)

 (b)

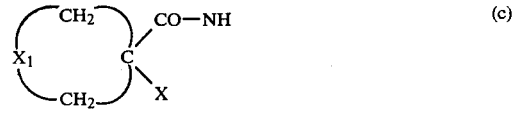 (c)

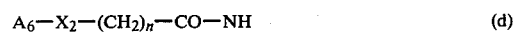 (d)

wherein n is 0, 1 or 2; m is 0, 1 or 2; $A_5$ is alkyl or 1 to 6 carbon atoms, cycloalkyl of 3 to 6 carbon atoms, cyclohexenyl, cyclohexadienyl, phenyl, hydroxyphenyl, thienyl or pyridyl; X is hydrogen, bromo, chloro, a carboxylic acid moiety, a carboxylate ester cleavable by hydrogenolysis or hydrolyzable in-vivo, hydroxy, acyloxy, amino, ureido, guanidino or acylureido; $A_6$ is phenyl, 2,5-dimethoxyphenyl, 2-alkoxy-1-naphthyl, 3-arylisoxazolyl, isothiazolyl or 3-aryl-5-methylisoxazolyl wherein aryl is phenyl; $X_1$ is $CH_2OCH_2$, $CH_2SCH_2$ or $(CH_2)_n$ wherein n is as above defined; and $X_2$ is an oxygen or sulphur atom, and E is a carboxy group, a pharmaceutically acceptable salt thereof, an alkyl ester thereof wherein the alkyl moiety is of 1 to 10 carbon atoms and is unsubstituted or substituted by alkoxy of 1 to 7 carbon atoms, alkanoyloxy of 1 to 7 carbon atoms, alkenyl of up to 5 carbon atoms or alkynyl of up to 5 carbon atoms, or by 1 or 2 phenyl moieties each of which is unsubstituted or substituted by fluoro, chloro, bromo, nitro, alkyl of up to 4 carbon atoms or alkoxy of up to 4 carbon atoms, or E is cyano, in combination with a pharmaceutically acceptable carrier.

35. A composition according to claim 34 wherein E is alkoxycarbonyl of 1 to 10 carbon atoms unsubstituted or substituted by alkoxy of 1 to 7 carbon atoms, alkanoyloxy of 1 to 7 carbon atoms, alkenyl of up to 5 carbon atoms or alkynyl of up to 5 carbon atoms, or by 1 or 2 phenyl moieties each of which is unsubstituted or substituted by fluoro, chloro, bromo, nitro, alkyl of up to 4 carbon atoms or alkoxy of up to 4 carbon atoms or E is cyano.

36. A composition according to claim 35 wherein E is a group of the sub-formula (L) or (M):

$CO_2B_1$  (L)

$CO_2CHB_2B_3$  (M)

wherein $B_1$ is alkyl of 1 to 6 carbon atoms unsubstituted or substituted by alkoxy of 1 to 7 carbon atoms or alkanoyloxy of 1 to 7 carbon atoms, $B_2$ is alkenyl of up to 5 carbon atoms, alkynyl of up to 5 carbon atoms or phenyl unsubstituted or substituted by fluoro, chloro, bromo, nitro or alkyl or alkoxy of up to 4 carbon atoms; and $B_3$ is hydrogen, alkyl of up to 4 carbon atoms or phenyl unsubstituted or substituted by fluoro, chloro, bromo, nitro or alkyl or alkoxy or up to 4 carbon atoms.

37. A composition according to claim 36 wherein E is methoxycarbonyl.

38. A composition according to claim 35 wherein E is cyano.

39. A composition according to claim 34 wherein RCONH is a group of the sub-formula (e) or (f):

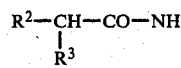 (e)

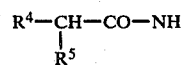 (f)

wherein $R^2$ is phenyl, thienyl or phenoxy; $R^3$ is hydrogen or methyl; $R^4$ is phenyl, p-hydroxyphenyl, thienyl or cyclohexadienyl; and $R^5$ is hydroxy, amino, a carboxylic acid moiety, phenyl, methylphenyl, indanyl or an alkyl ester thereof of 1 to 6 carbon atoms.

40. A compound according to claim 39 wherein RCONH is phenoxyacetamido, phenylacetamido, α-aminophenylacetamido or α-carboxyphenylacetamido.

41. A composition according to claim 36 wherein $B_1$ is alkyl of 1 to 6 carbon atoms.

42. A composition according to claim 36 wherein $B_1$ is methyl, ethyl, propyl, isopropyl, butyl, isobutyl, sec-butyl, tert-butyl, pentyl, neopentyl, isopentyl or hexyl.

43. A composition according to claim 36 wherein $B_1$ is methyl, ethyl or propyl.

44. A composition according to claim 36 wherein $B_1$ is methyl.

45. A composition according to claim 36 wherein $B_3$ is hydrogen and $B_2$ is phenyl unsubstituted or substituted by fluoro, chloro, bromo, nitro, alkyl of up to 4 carbon atoms or alkoxy of up to 4 carbon atoms.

46. A composition according to claim 36 wherein $CHB_2B_3$ is benzyl, methoxybenzyl, ethoxybenzyl, nitrobenzyl or chlorobenzyl.

47. A composition according to claim 34 wherein RCONH is phenylacetamido, p-hydroxyphenylacetamido, o-hydroxyphenylacetamido, m-hydroxyphenylacetamido, α-chlorophenylacetamido, α-bromophenylacetamido, α-carboxyphenylacetamido or the methylphenyl, indanyl or phenyl ester thereof, α-azidophenylacetamido, α-aminophenylacetamido, α-hydroxyphenylacetamido, α-ureidophenylacetamido, α-guanidinophenylacetamido, α-(acetylureido)-phenylacetamido, α-acetoxyphenylacetamido, α-tetrazolylphenylacetamido, acetamido, chloroacetamido, bromoacetamido, propionamido, pyridylacetamido, 2-thienylacetamido, 3-thienylacetamido, 2-thienylpropionamido, 3-thienylpropionamido, α-chloro(p-hydroxyphenyl)acetamido, α-bromo(p-hydroxyphenyl)acetamido, α-carboxy(p-hydroxyphenyl)acetamido or the methyl, phenyl, indanyl or phenyl ester thereof, α-amino(p-hydroxyphenyl)acetamido, α-hydroxy(p-hydroxyphenyl)acetamido, α-acetoxy(p-hydroxyphenyl)acetamido, α-ureido(p-hydroxyphenyl)acetamido, α-guanidino(p-hydroxyphenyl)acetamido, α-acetylureido(p-hydroxyphenyl)acetamido, phenoxyacetamido, o-hydroxyphenoxyacetamido, m-hydroxyphenoxyacetamido, p-hydroxyphenoxyacetamido, methoxyacetamido, ethoxyacetamido, α-amino(p-hydroxy)phenoxyacetamido, α-aminophenoxyacetamido, α-acetylphenoxyacetamido, α-acetyl(p-hydroxy)-phenylacetamido, α-hydroxyphenoxyacetamido, α-hydroxy(p-hydroxy)-phenylacetamido, α-carboxyphenoxyacetamido or the methylphenyl, indanyl or phenyl ester thereof, α-carboxy(p-hydroxy)phenoxyacetamido or the methylphenyl, indanyl or phenyl ester thereof, phenoxypropionamido, phenoxybutyramido, benzamido, 2,6-dimethoxybenzamido, 2-ethoxy-1-naphthamido, 2-methoxy-1-naphthamido, 2-propoxy-1-naphthamido, 3-phenyl-5-methyl-4-isoxazolylcarboxamido, 3-o-chlorophenyl-5-methyl-4-isoxazolylcarboxamido, 3-o,o-dichlorophenyl-5-methyl-4-isoxazolylcarboxamido, isothiazolylcarboxamido, 3-o,o-fluorochlorophenyl-5-methyl-4-isoxazolylcarboxamido, 3-phenyl-4-isoxazolylcarboxamido, 3-o-chlorophenyl-4-isoxazolylcarboxamido, 3-o,o-dichlorophenyl-4-isoxazolylcarboxamido, 3-o,o-fluorochlorophenyl-4-isoxazolylcarboxamido, 1-aminocyclohexyl-1-carboxamido, phenylthioacetamido, phenylthiopropionamido or p-hydroxyphenylthioacetamido.

48. A composition according to claim 47 wherein RCONH is phenylacetamido.

49. A composition according to claim 34 wherein RCONH is α-methylphenoxyacetamido, α-methylphenylacetamido, α-methyl-2-thienylacetamido, α-methyl-3-thienylacetamido, 2-thienylacetamido, 3-thienylacetamido, α-hydroxyphenylacetamido, α-hydroxy(p-hydroxyphenyl)acetamido, α-hydroxy-2-thienylacetamido, α-hydroxy-3-thienylacetamido, α-aminophenylacetamido, α-amino(p-hydroxyphenyl)acetamido, α-amino-3-thienylacetamido, α-amino-2-thienylacetamido, α-carboxyphenylacetamido, α-carboxy(p-hydroxyphenyl)acetamido, α-carboxy-2-thienylacetamido, α-carboxy-3-thienylacetamido or the methyl, ethyl, propyl, butyl, phenyl, methylphenyl or indanyl ester of α-carboxyphenylacetamido, the methyl, ethyl, propyl, butyl, phenyl, methylphenyl or indanyl ester of α-carboxy(p-hydroxyphenylacetamido), the methyl, ethyl, propyl, butyl, phenyl, methylphenyl or indanyl ester of α-carboxy-2-thienylacetamido or the methyl, ethyl, propyl, butyl, phenyl, methylphenyl or indanyl ester of α-carboxy-3-thienylacetamido.

50. A composition according to claim 53 wherein the compound is of the formula (III):

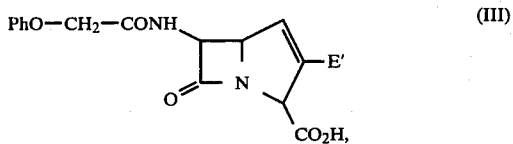

a pharmaceutically acceptable salt thereof or a cleavable ester thereof, wherein E' is methoxycarbonyl or cyano.

51. A composition according to claim 53 wherein the compound is of the formula (IV):

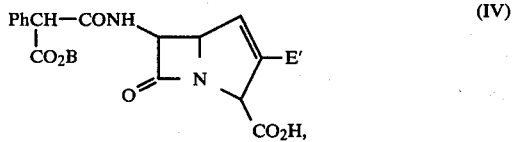

a pharmaceutically acceptable salt thereof or cleavable ester thereof, wherein E' is methoxycarbonyl or cyano and B is a cation, hydrogen, benzyl, phenyl, methylphenyl or indanyl.

52. A composition according to claim 53 wherein the compound is of the formula (V):

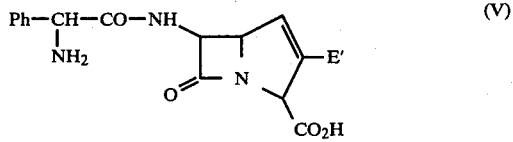

a pharmaceutically acceptable salt thereof or a cleavable ester thereof, wherein E' is methoxycarbonyl or cyano.

53. A composition according to claim 34 wherein the compound is in the form of a pharmaceutically acceptable salt wherein said salt is an aluminum, sodium, potassium, calcium, magnesium, ammonium or substituted ammonium salt.

54. A composition according to claim 53 wherein the salt is the p-toluidine salt.

55. A composition according to claim 53 wherein the salt is the sodium, potassium, calcium or magnesium salt.

56. A composition according to claim 53 wherein the salt is the sodium salt.

57. A composition according to claim 53 wherein the salt is the potassium salt.

58. A composition according to claim 34 wherein the compound is in the form of the free acid.

59. A composition according to claim 34 wherein the compound is in zwitterionic form.

60. A composition according to claim 34 wherein the compound is in the form of a di-acid.

61. A composition according to claim 34 wherein the compound is in the form of a di-pharmaceutically acceptable salt.

62. A composition according to claim 34 wherein the compound is in the form of an ester wherein the ester is a benzyl ester wherein the phenyl moiety is unsubstituted or substituted by alkyl of 1 to 6 carbon atoms, alkoxy of 1 to 6 carbon atoms, chloro, bromo or nitro.

63. A composition according to claim 34 wherein the compound is in the form of an ester wherein the ester is the p-nitrobenzyl ester.

64. A composition according to claim 34 wherein the compound is in the form of an ester wherein the ester is of the sub-formulae (g), (h) or (j):

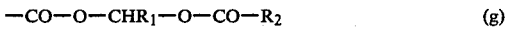
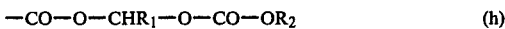
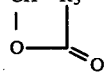

wherein $R_1$ is hydrogen or methyl; $R_2$ is alkyl of up to 4 carbon atoms, phenyl or benzyl; and $R_3$ is —CH═CH—, 1,2-phenylene or 4,5-dimethoxy-1,2-phenylene.

65. A composition according to claim 34 wherein the compound is in the form of an ester wherein the ester is the acetoxymethyl, pivaloyloxymethyl, α-acetoxyethyl, α-pivaloyloxyethyl, α-ethoxycarbonyloxyethyl, phthalidyl or 3,4-dimethoxyphthalidyl.

66. An ester according to claim 65 wherein the ester is phthalidyl.

67. A method of treating bacterial infections in animals including humans which comprises administering to such an animal in need thereof, an antibacterially effective amount of a compound of the formula (II):

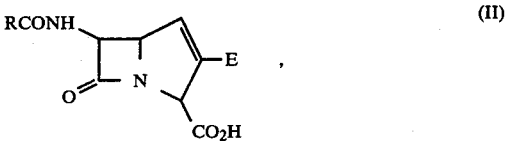

a pharmaceutically acceptable salt thereof or an ester thereof cleavable by hydrogenolysis or hydrolyzable in-vivo wherein RCONH is a group of the sub-formula (a), (b), (c) or (d):

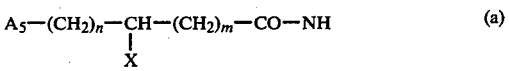

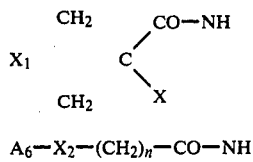  (c)

A₆—X₂—(CH₂)ₙ—CO—NH   (d)

wherein n is 0, 1 or 2; m is 0, 1 or 2; $A_5$ is alkyl of 1 to 6 carbon atoms, cycloalkyl of 3 to 6 carbon atoms, cyclohexenyl, cyclohexadienyl, phenyl, hydroxyphenyl, thienyl or pyridyl; X is hydrogen, bromo, chloro, a carboxylic acid moiety, a carboxylate ester cleavable by hydrogenolysis or hydrolyzable in-vivo, hydroxy, acyloxy, amino, ureido, guanidino or acylureido; $A_6$ is phenyl, 2,5-dimethoxyphenyl, 2-alkoxy-1-naphthyl, 3-arylisoxazolyl, isothiazolyl or 3-aryl-5-methylisoxazolyl wherein aryl is phenyl; $X_1$ is $CH_2OCH_2$, $CH_2SCH_2$ or $(CH_2)_n$ wherein n is as above defined; and $X_2$ is an oxygen or sulphur atom, and E is a carboxy group, a pharmaceutically acceptable salt thereof, an alkyl ester thereof wherein the alkyl moiety is of 1 to 10 carbon atoms and is unsubstituted or substituted by alkoxy of 1 to 7 carbon atoms, alkanoyloxy of 1 to 7 carbon atoms, alkenyl of up to 5 carbon atoms or alkynyl of up to 5 carbon atoms, or by 1 or 2 phenyl moieties each of which is unsubstituted or substituted by fluoro, chloro, bromo, nitro, alkyl of up to 4 carbon atoms or alkoxy of up to 4 carbon atoms, or E is cyano, in combination with a pharmaceutically acceptable carrier.

68. A method according to claim 67 wherein E is alkoxycarbonyl of 1 to 10 carbon atoms unsubstituted or substituted by alkoxy of 1 to 7 carbon atoms, alkanoyloxy of 1 to 7 carbon atoms, alkenyl of up to 5 carbon atoms or alkynyl of up to 5 carbon atoms, or by 1 or 2 phenyl moieties each of which is unsubstituted or substituted by fluoro, chloro, bromo, nitro, alkyl of up to 4 carbon atoms or alkoxy of up to 4 carbon atoms or E is cyano.

69. A method according to claim 68 wherein E is a group of the sub-formula (L) or (M):

 (L)

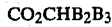 (M)

wherein $B_1$ is alkyl of 1 to 6 carbon atoms unsubstituted or substituted by alkoxy of 1 to 7 carbon atoms or alkanoyloxy of 1 to 7 carbon atoms, $B_2$ is alkenyl of up to 5 carbon atoms, alkynyl of up to 5 carbon atoms or phenyl unsubstituted or substituted by fluoro, chloro, bromo, nitro or alkyl or alkoxy of up to 4 carbon atoms; and $B_3$ is hydrogen, alkyl of up to 4 carbon atoms or phenyl unsubstituted or substituted by fluoro, chloro, bromo, nitro or alkyl or alkoxy or up to 4 carbon atoms.

70. A method according to claim 69 wherein E is methoxycarbonyl.

71. A method according to claim 68 wherein E is cyano.

72. A method according to claim 67 wherein RCONH is a group of the sub-formula (e) or (f):

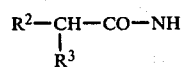 (e)

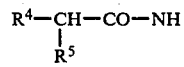 (f)

wherein $R^2$ is phenyl, thienyl or phenoxy; $R^3$ is hydrogen or methyl; $R^4$ is phenyl, p-hydroxyphenyl, thienyl or cyclohexadienyl; and $R^5$ is hydroxy, amino, a carboxylic acid moiety, phenyl, methylphenyl, indanyl or an alkyl ester thereof of 1 to 6 carbon atoms.

73. A method according to claim 72 wherein RCONH is phenoxyacetamido, phenylacetamido, α-aminophenylacetamido or α-carboxyphenylacetamido.

74. A method according to claim 69 wherein $B_1$ is alkyl of 1 to 6 carbon atoms.

75. A method according to claim 69 wherein $B_1$ is methyl, ethyl, propyl, isopropyl, butyl, isobutyl, sec-butyl, tert-butyl, pentyl, neopentyl, isopentyl or hexyl.

76. A method according to claim 69 wherein $B_1$ is methyl, ethyl or propyl.

77. A method according to claim 69 wherein $B_1$ is methyl.

78. A method according to claim 69 wherein $B_3$ is hydrogen and $B_2$ is phenyl unsubstituted or substituted by fluoro, chloro, bromo, nitro, alkyl of up to 4 carbon atoms or alkoxy of up to 4 carbon atoms.

79. A method according to claim 69 wherein $CHB_2B_3$ is benzyl, methoxybenzyl, ethoxybenzyl, nitrobenzyl or chlorobenzyl.

80. A method according to claim 67 wherein RCONH is phenylacetamido, p-hydroxyphenylacetamido, o-hydroxyphenylacetamido, m-hydroxyphenylacetamido, α-chlorophenylacetamido, α-bromophenylacetamido, α-carboxyphenylacetamido or the methylphenyl, indanyl or phenyl ester thereof, α-azidophenylacetamido, α-aminophenylacetamido, α-hydroxyphenylacetamido, α-ureidophenylacetamido, α-guanidinophenylacetamido, α-(acetylureido)-phenylacetamido, α-acetoxyphenylacetamido, α-tetrazolylphenylacetamido, acetamido, chloroacetamido, bromoacetamido, propionamido, pyridylacetamido, 2-thienylacetamido, 3-thienylacetamido, 2-thienylpropionamido, 3-thienylpropionamido, α-chloro(p-hydroxyphenyl)acetamido, α-bromo(p-hydroxyphenyl)acetamido, α-carboxy(p-hydroxyphenyl)acetamido or the methyl, phenyl, indanyl or phenyl ester thereof, α-amino(p-hydroxyphenyl)acetamido, α-hydroxy(p-hydroxyphenyl)acetamido, α-acetoxy(p-hydroxyphenyl)acetamido, α-ureido(p-hydroxyphenyl)acetamido, α-guanidino(p-hydroxyphenyl)acetamido, α-acetylureido(p-hydroxyphenyl)acetamido, phenoxyacetamido, o-hydroxyphenoxyacetamido, m-hydroxyphenoxyacetamido, p-hydroxyphenoxyacetamido, methoxyacetamido, ethoxyacetamido, α-amino(p-hydroxy)phenoxyacetamido, α-aminophenoxyacetamido, α-acetylphenoxyacetamido, α-acetyl(p-hydroxy)-phenylacetamido, α-hydroxyphenoxyacetamido, α-hydroxy(p-hydroxy)-phenylacetamido, α-carboxyphenoxyacetamido or the methylphenyl, indanyl or phenyl ester thereof, α-carboxy(p-hydroxy)phenoxyacetamido or the methylphenyl, indanyl or phenyl ester thereof, phenoxypropionamido, phenoxybutyramido, benzamido, 2,6-dimethoxybenzamido, 2-ethoxy-1-naphthamido, 2-methoxy-1-naphthamido, 2-propoxy-1-naphthamido, 3-phenyl-5-methyl-4-isoxazolylcarboxamido, 3-o-chlorophenyl-5-methyl-4-isoxazolylcarboxamido, 3-o,o-dichlorophenyl-5-methyl-4-isoxazolylcarboxamido, isothiazolylcarboxamido, 3- o,o-fluorochlorophenyl-5-methyl-4-isoxazolylcarboxamido, 3-phenyl-4-isoxazolylcarboxamido, 3-o-chlorophenyl-4-isoxazolyl-carboxamido, 3-o,o-dichlorophenyl-4-isoxazolylcarboxamido, 3-o,o-fluorochlorophenyl-4-isoxazolylcarboxamido, 1-aminocyclohexyl-1-carboxamido, phenylthioacetamido, phenylthiopropionamido or p-hydroxyphenylthioacetamido.

81. A method according to claim 80 wherein RCONH is phenylacetamido.

82. A method according to claim 67 wherein RCONH is α-methylphenoxyacetamido, α-methylphenylacetamido, α-methyl-2-thienylacetamido, α-methyl-3-thienylacetamido, 2-thienylacetamido, 3-thienylacetamido, α-hydroxyphenylacetamido, α-hydroxy(p-hydroxyphenyl)acetamido, α-hydroxy-2-thienylacetamido, α-hydroxy-3-thienylacetamido, α-aminophenylacetamido, α-amino(p-hydroxyphenyl)acetamido, α-amino-3-thienylacetamido, α-amino-2-thienylacetamido, α-carboxyphenylacetamido, α-carboxy(p-hydroxyphenyl)acetamido, α-carboxy-2-thienylacetamido, α-carboxy-3-thienylacetamido or the methyl, ethyl, propyl, butyl, phenyl, methylphenyl or indanyl ester of α-carboxyphenylacetamido, the methyl, ethyl, propyl, butyl, phenyl, methylphenyl or indanyl ester of α-carboxy(p-hydroxyphenylacetamido), the methyl, ethyl, propyl, butyl, phenyl, methylphenyl or indanyl ester of α-carboxy-2-thienylacetamido or the methyl, ethyl, propyl, butyl, phenyl, methylphenyl or indanyl ester of α-carboxy-3-thienylacetamido.

83. A method according to claim 67 wherein the compound is of the formula (III):

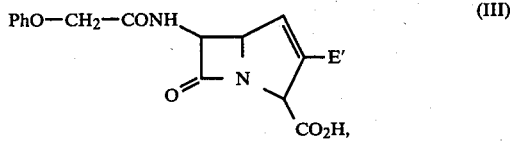

(III)

a pharmaceutically acceptable salt thereof or a cleavable ester thereof, wherein E' is methoxycarbonyl or cyano.

84. A method according to claim 67 wherein the compound is of the formula (IV):

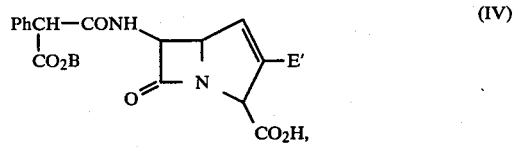

(IV)

a pharmaceutically acceptable salt thereof or cleavable ester thereof, wherein E' is methoxycarbonyl or cyano and B is a cation, hydrogen, benzyl, phenyl, methylphenyl or indanyl.

85. A method according to claim 67 wherein the compound is of the formula (V):

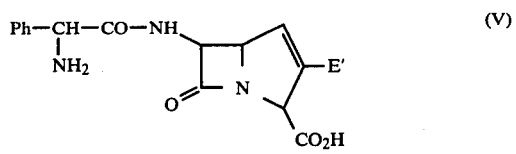

(V)

a pharmaceutically acceptable salt thereof or a cleavable ester thereof, wherein E' is methoxycarbonyl or cyano.

86. A method according to claim 67 wherein the compound is in the form of a pharmaceutically acceptable salt wherein said salt is an aluminum, sodium, potassium, calcium, magnesium, ammonium or substituted ammonium salt.

87. A method according to claim 86 wherein the salt is the p-toluidine salt.

88. A method according to claim 86 wherein the salt is the sodium, potassium, calcium or magnesium salt.

89. A method according to claim 86 wherein the salt is the sodium salt.

90. A method according to claim 86 wherein the salt is the potassium salt.

91. A method according to claim 67 wherein the compound is in the form of the free acid.

92. A method according to claim 67 wherein the compound is in zwitterionic form.

93. A method according to claim 67 wherein the compound is in the form of a di-acid.

94. A method according to claim 67 wherein the compound is in the form of a di-pharmaceutically acceptable salt.

95. A method according to claim 67 wherein the compound is in the form of an ester wherein the ester is a benzyl ester wherein the phenyl moiety is unsubstituted or substituted by alkyl of 1 to 6 carbon atoms, alkoxy of 1 to 6 carbon atoms, chloro, bromo or nitro.

96. A method according to claim 67 wherein the compound is in the form of an ester wherein the ester is the p-nitrobenzyl ester.

97. A method according to claim 67 wherein the compound is in the form of an ester wherein the ester is of the sub-formulae (g), (h) or (j):

—CO—O—CHR$_1$—O—CO—R$_2$ (g)

—CO—O—CHR$_1$—O—CO—OR$_2$ (h)

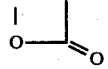 (j)

wherein R$_1$ is hydrogen or methyl; R$_2$ is alkyl of up to 4 carbon atoms, phenyl or benzyl; and R$_3$ is —CH═CH—, 1,2-phenylene or 4,5-dimethoxy-1,2-phenylene.

98. A method according to claim 67 wherein the compound is in the form of an ester wherein the ester is the acetoxymethyl, pivaloyloxymethyl, α-acetoxyethyl, α-pivaloyloxyethyl, α-ethoxycarbonyloxyethyl, phthalidyl or 3,4-dimethoxyphthalidyl.

99. An ester according to claim 99 wherein the ester is phthalidyl.

100. A composition according to claim 34 in oral administration form.

101. A composition according to claim 34 in a form suitable for administration by injection or infusion.

102. A method according to claim 67 wherein the administration is oral.

103. A method according to claim 67 wherein the administration is by injection or infusion.

* * * * *